United States Patent [19]
Smith et al.

[11] Patent Number: 5,954,959
[45] Date of Patent: Sep. 21, 1999

[54] MICRODIALYSIS UNIT FOR MOLECULAR WEIGHT SEPARATION

[75] Inventors: Richard D. Smith; Chuanliang Liu, both of Richland, Wash.

[73] Assignee: Battelle Memorial Institute, Richland, Wash.

[21] Appl. No.: 08/855,727

[22] Filed: May 9, 1997

[51] Int. Cl.$^6$ .......................... B01D 61/28; B01D 63/02
[52] U.S. Cl. ................. 210/321.78; 210/259; 210/321.6; 210/321.87
[58] Field of Search ........................ 210/321.6, 321.72, 210/321.78, 321.87, 259, 500.23; 422/44, 50

[56] References Cited

U.S. PATENT DOCUMENTS

| | | | |
|---|---|---|---|
| 3,442,389 | 5/1969 | Mendelson | 210/321.81 |
| 4,491,011 | 1/1985 | Nordmeyer et al. | 210/656 |
| 4,781,889 | 11/1988 | Fukasawa et al. | 210/321.8 |
| 4,794,088 | 12/1988 | Miyaki et al. | 210/656 |
| 4,804,628 | 2/1989 | Cracauer et al. | 210/321.8 |
| 4,921,952 | 5/1990 | Longmire et al. | 536/27 |
| 5,078,135 | 1/1992 | Caprioli | 128/632 |
| 5,202,023 | 4/1993 | Trimmer et al. | 210/321.8 |
| 5,449,064 | 9/1995 | Hogan et al. | 204/193 |
| 5,492,838 | 2/1996 | Pawliszyn | 210/321.8 |
| 5,572,023 | 11/1996 | Caprioli | 250/288 |
| 5,706,806 | 1/1998 | Kissinger | 128/632 |

*Primary Examiner*—John Kim
*Attorney, Agent, or Firm*—Paul W. Zimmerman

[57] ABSTRACT

The present invention relates generally to an apparatus and method for separating high molecular weight molecules from low molecular weight molecules. More specifically, the invention relates to the use of microdialysis for removal of the salt (low molecular weight molecules) from a nucleotide sample (high molecular weight molecules) for ESI-MS analysis. The dialysis or separation performance of the present invention is improved by (1) increasing dialysis temperature thereby increasing desalting efficiency and improving spectrum quality; (2) adding piperidine and imidazole to the dialysis buffer solution and reducing charge states and further increasing detection sensitivity for DNA; (3) using low concentrations (0–2.5 mM NH4OAc) of dialysis buffer and shifting the DNA negative ions to higher charge states, producing a nearly 10-fold increase in detection sensitivity and a slightly decreased desalting efficiency, or (4) any combination of (1), (2), and (3).

11 Claims, 14 Drawing Sheets

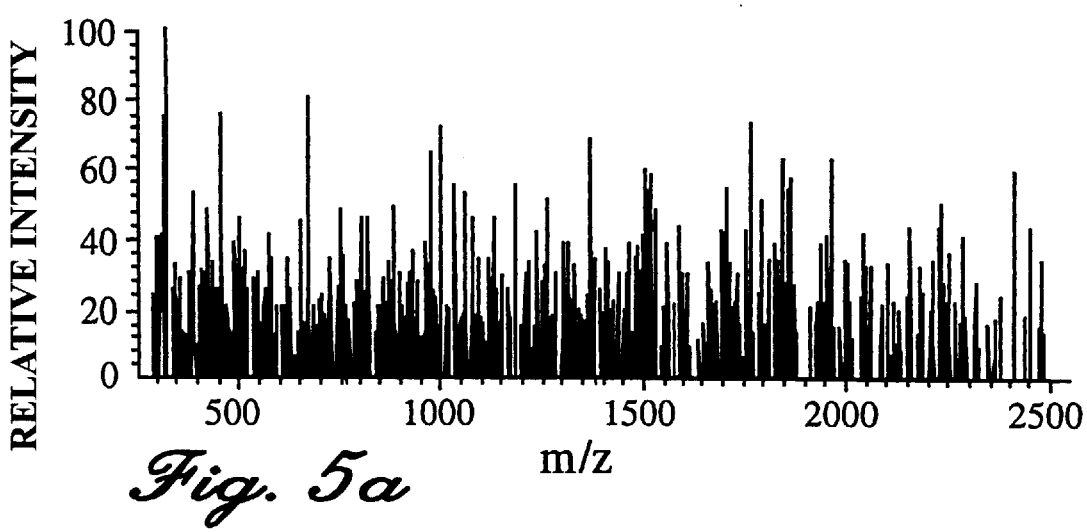
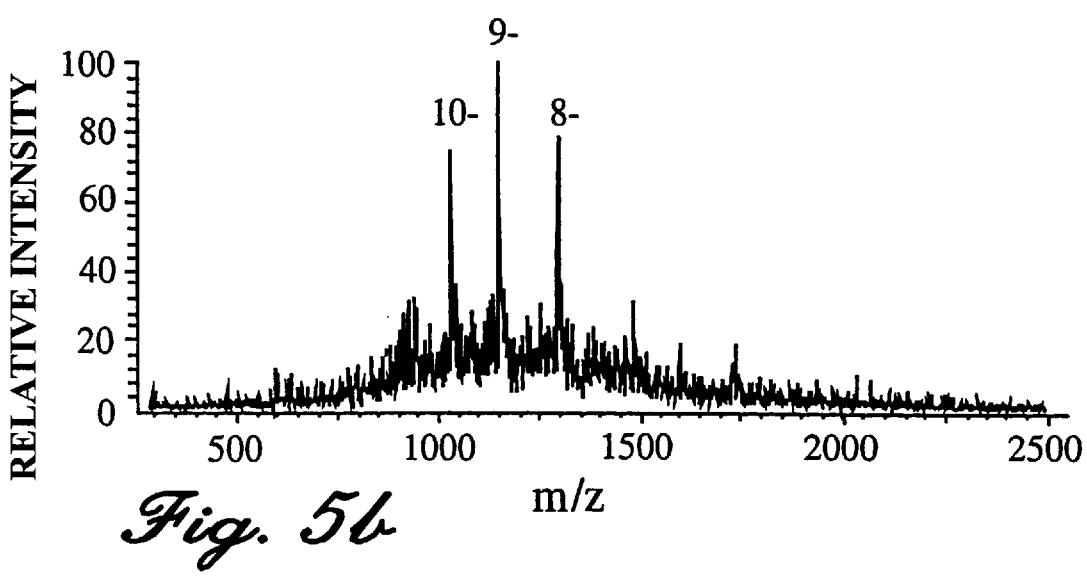
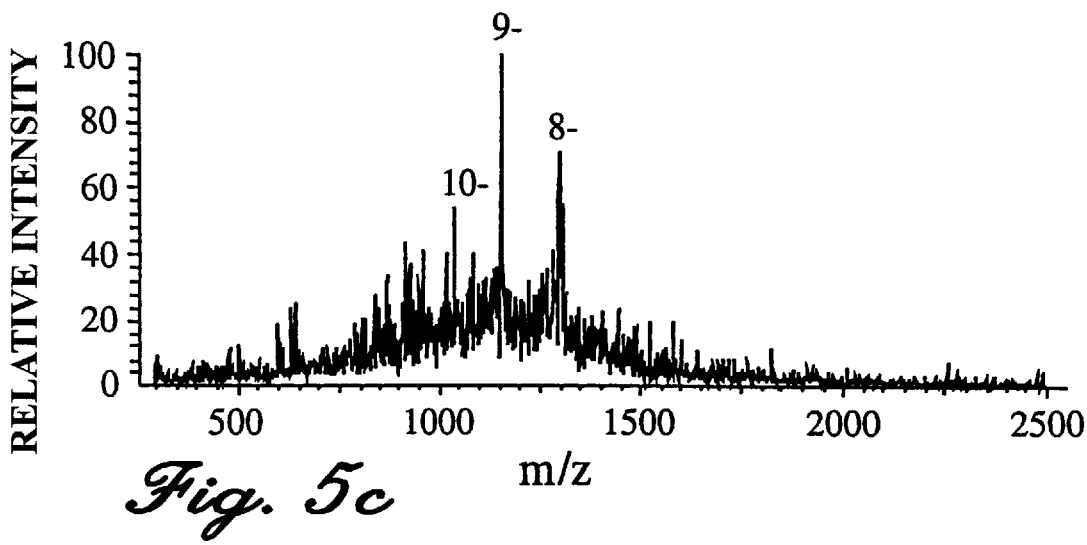

MICRODIALYSIS UNIT FOR MOLECULAR WEIGHT SEPARATION

This invention was made with Government support under Contract DE-AC06-76RLO 1830 awarded by the U.S. Department of Energy. The Government has certain rights in the invention.

FIELD OF THE INVENTION

The present invention relates generally to an apparatus and method for separating biomolecules and other high molecular weight compounds from low molecular weight molecules. More specifically, the invention relates to the use of microdialysis for separation and removal of the salt (low molecular weight molecules) from biomolecules in a biological sample for subsequent analysis. As used herein, the term biomolecule includes but is not limited to carbohydrates, glycoproteins, peptides, nucleotides oligonucleotides, oligonucleotide duplexes, quadruplexes, and DNA-protein complexes, DNA segment, proteins, synthetic polymers biopolymers and combinations thereof. As used herein, the term low molecular weight molecule includes salts as well as other molecules with a molecular weight less than a thousand daltons, for example ionic species as well as multi-element compounds.

BACKGROUND OF THE INVENTION

The use of electrospray ionization-mass spectrometry (ESI-MS) has increased for characterizing biomolecules, for example proteins and oligonucleotides as well as other high molecular weight compounds. Collisional induced dissociation methods have provided information on amino acid and nucleotide sequence and sites of damage or modification. ESI-MS has been more recently used for analysis of non-covalent complexes including oligonucleotide duplexes, quadruplexes, and DNA-protein complexes, and probing the higher order structure of proteins. However, biological samples prepared under physiological conditions typically contain significant concentrations of salts (e.g., sodium chloride) as well as other non-volatile reagents added to stabilize samples or to maintain their enzymatic activity. The presence of small to moderate amounts of sodium salts, for example, affects electrospray stability due to changes in solution conductivity, and may significantly reduce the detected analyte ion abundance due to both suppression of ionization and the formation of multiple species having sodium adducts. Low signal-to-noise ratios of the mass spectra and poor reproducibility due to excessive adduction can result in inaccurate mass assignments and, in severe cases, even preclude spectrum interpretation.

Sodium adduct formation is attributed primarily to electrostatic interactions of sodium ions with negatively charged sites on the high molecular weight molecules, e.g. phosphate groups on the polynucleotide backbone in DNA. Large DNA molecules have a proportionally higher affinity for sodium ion because of the extended polynucleotide backbone. Therefore, removal of sodium ion from large DNA molecules to the levels required to produce high quality spectra is more difficult than for small oligonucleotides.

Various methods have been used to reduce cation adduction and other types of problematic contamination due to low MW species. A common approach is the multiple buffer exchange method using a membrane cartridges. The salt-containing sample is repeatedly diluted with ammonium acetate buffer and concentrated by centrifugation, resulting in a decreased salt concentration. This process, although simple in nature, typically requires several hours and often results in significant sample losses which greatly limits its analytical capability for limited sample sizes. The desalting efficiency of this technique is very low for DNA samples due to the high affinity of DNA molecules for sodium, and significant cation adduct ions are still present even after more than five cycles of buffer exchange.

Although on-line LC/MS can tolerate small to moderate amounts of salt, and desalting columns are commercially available, they are not suitable for many ESI-MS experiments where samples may precipitate on the column, interact with the solvent, or when very high salt concentrations are present. It is less effective for desalting of large oligonucleotides.

Stults and Marsters, Rapid Commun. Mass Spectrom. 1991, 5, 359–363, reported an ammonium acetate precipitation method that reduced the sodium adduction for oligonucleotides up to 77-mer in length thereby improving the mass spectrum quality. This method was performed off-line, separately from the ESI-MS, required large amount of sample to overcome significant sample loss during the precipitation step. The ammonium acetate method has been shown to be less effective for desalting of larger (>60-mer in size) DNA or RNA molecules.

Nordhoff et al., Rapid Commun. Mass Spectrom. 1992, 6, 771–776, described another off-line method of sodium removal by using cation exchange polymer beads, which was limited to oligonucleotide samples with low concentrations of cation contamination.

Emmett and Capioli, J. Am. Soc. Mass Spectrom. 1994, 5, 605–613, reported an on-line micro-LC (liquid chromatography) sample clean-up method using a C18 cartridge stationary phase that suffered from the disadvantages of HPLC desalting and the difficulties of packing the capillary columns.

Greig and Griffey, Rapid Commun. Mass Sepctrom. 1995, 9, 97–102, used organic bases, 25 mM piperidine and 25 mM imidazole, to suppress adduct formation or cation adduction in ESI-MS of oligonucleotide samples. But, the salt concentration tolerance of this method is relatively low (<<10 mM salt or cation). Further compensating for high salt concentration by addition of higher concentrations of organic bases (>50 mM) resulted in greatly decreased detection sensitivity. In addition, some modified DNA and RNA molecules (e.g. DNA/drug or RNA/drug adduct) are not stable under these basic conditions.

Cheng et al., Anal. Chem. 1995, 67, 586–593, used inorganic acids and bases. Addition of organic or inorganic acids (or bases) is useful for smaller oligonucleotides, but not for larger oligonucleotides since they can alter the native conformation of DNA molecules which is undesirable for studies requiring a native DNA conformation. These methods of salt removal are useful only for salt concentrations less than about 25 mM.

Dialysis has been used for clean-up of biopolymers for removal of low molecular weight contaminants including salts. However, conventional "batch" dialysis methods require large amount of samples, proceed for several hours and incur significant sample loss. When only a small amount of sample is available, sample loss can become even more pronounced. If non-covalent association are of interest, slow desalting in conventional dialysis is more likely to result in denaturation and/or complex dissociation in solution.

Thus, there remains a need for an apparatus and method for removing contaminants from biomolecular samples that preserves the biomolecules and operates in a short time.

SUMMARY OF THE INVENTION

The present invention is a new and efficient apparatus and method for the rapid separation of low molecular weight molecules from high molecular weight molecules in samples that include biomolecules and/or other high molecular weight compounds. While the present invention is particularly useful for desalting of oligonucleotides for ESI-MS studies, it is broadly applicable to desalting of other large molecular weight molecules such as carbohydrates, glycoproteins, peptides, nucleotides oligonucleotides, oligonucleotide duplexes, quadruplexes, and DNA-protein complexes, DNA segment, proteins, synthetic polymers, natural products and combinations thereof; and for all other mass spectrometric techniques, as well as any other technique in which sample desalting is desirable. Analytical techniques, for example ESI-MS have sample flow rates ranging from a few nanoliters per minute to milliliters per minute, and for ESI-MS specifically, sensitivity increases with decreasing flow rate. Accordingly, the present invention, useful across the flow rate range, has been specifically demonstrated at low flow rates from about 2 $\mu$L/min to about 100 nL/min.

The present invention uses a capillary size dialysis fiber to increase sample surface to volume ratio and a counter-current dialysis buffer flow to increase buffer exchange rate. It has demonstrated essentially complete salt removal in <5 minutes at sodium chloride concentrations of as high as 250 mM, compared to several hours for conventional dialysis. Thus, there is a surprising 2500× improvement in separation/desalting time for only a 50× reduction in dialysis tube diameter. The advantages of separating the low molecular weight molecules (salt) include (1) an increase in the signal-to-noise ratio of a factor of more than 40 times for ESI-MS analysis compared to that obtained without low molecular weight molecule separation, and (2) greater accuracy in molecular weight measurements. It will be apparent to those of skill in the art of large molecule analysis, that the present invention is not limited to the biomolecules of variable size and sequence demonstrated herein, but is useful for other biological samples, synthetic polymers, and natural products as well. The fast dialysis rate combined with the pH neutral dialysis buffer also enables the preservation of non-covalent associations. The present invention specifically and especially has greatly improved the routine application of ESI-MS in DNA analysis, and has also be demonstrated use for samples that display limited stability after desalting.

Initial results for oligonucleotides and proteins of various sizes have indicated broad applicability of this method. Detection of subpicomole samples of a 34-mer oligonucleotide and apomyoglobin having high salt concentrations was also achieved. Desalting was completed in one to four minutes for the samples with up to 250 mM of NaCl for DNA and 1.3 M for proteins, which conventionally required several hours using alternative off-line desalting schemes. Although a low sample infusion rate of 2–5 $\mu$l/min was required for these initial studies, the micro-source electrospray was stable. Lower sample infusion rate and lower detection limits are achievable with further development of the method, including the use of dialysis tubes having smaller diameters. Alternatively, sample "plugs" may be used to achieve dialysis of very small samples.

While the present results obtained at neutral pH conditions preserve the native conformation of the high molecular weight molecules and their noncovalent complexes with ligands, lower pH buffer may also be used to denature (unfold) some large proteins and to increase the efficiency of desalting if a native structure is not required.

The apparatus and method of the present invention may be used on-line or off-line with respect to any subsequent analytical method or instrumentation. When used on-line, on-line coupling of microdialysis with, for example, ESI-MS is facile due to the liquid interface. When used off-line, the present invention demonstrated a similar increase in desalting efficiency, compared with conventional centrifugation or other off-line batch-mode dialysis methods. The effectiveness of the desalting is ascribed to both the small diameter of dialysis tube used, and the fact that the protein sample solution is much more effectively exposed to the dialysis buffer which is continuously refreshed by the counter flow. A more than 10-fold decrease in sample consumption was achieved using the off-line mode vs. on-line mode which resulted in a similar quality spectrum. The sample flow rate in an off-line mode may be decreased to permit longer dialysis time for desalting of samples with complicated matrices, without the flow rate limitations encountered in the on-line mode.

Whether on-line or off-line, the dialysis or separation performance may be improved by (1) increasing dialysis temperature thereby increasing desalting efficiency and improving spectrum quality; (2) adding piperidine and imidazole to the dialysis buffer solution and reducing charge states and further increasing detection sensitivity for DNA; (3) using low concentrations (0–2.5 mM NH4OAc) of dialysis buffer and shifting the DNA negative ions to higher charge states, producing a nearly 10-fold increase in detection sensitivity and a slightly decreased desalting efficiency, or (4) any combination of (1), (2), and (3). These performance improvements extend the applicability of the present invention especially for biomolecular analyses (and other analyses) requiring rapid and complete desalting.

The present invention has several advantages over the present state of the art in separating low molecular weight molecules from high molecular weight molecules for analysis. The advantages include (1) faster separation (e.g. desalting) speed, (2) greater separation (e.g. desalting) efficiency, (3) smaller sample volume requirement, (4) preservation of native DNA and peptide conformation when a pH neutral dialysis buffer is used, (5) capability dialysis on-line or in-line with an analytical instrument, and (6) reduced buffer consumption, in some cases more than an order of magnitude less buffer than present desalting methods.

It is an object of the present invention to provide a microdialysis unit for separating low molecular weight molecules from high molecular weight molecules at a faster rate than present separation devices.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

BRIEF DESCRIPTION OF THE DRAWING

FIG. 2a(I) is an inset showing an expanded view of the 5– charge state showing multiple sodium adduct ions from FIG. 2a.

FIG. 2b(I) is an inset showing an expanded view of the 5-charge state showing the effective removal of sodium adduction from FIG. 2b.

FIG. 5a is a mass spectrum of oligonucleotide #4 in 10 $\mu$M NH$_4$OAc from direct infusion.

FIG. 5b is a mass spectrum of oligonucleotide #4 in 10 mM NH$_4$OAc after on-line microdialysis.

FIG. 5c is a mass spectrum of oligonucleotide #4 in 10 mM NH$_4$OAc and 250 mM NaCl after on-line microdialysis.

DESCRIPTION OF THE PREFERRED EMBODIMENT(S)

Figure 1:
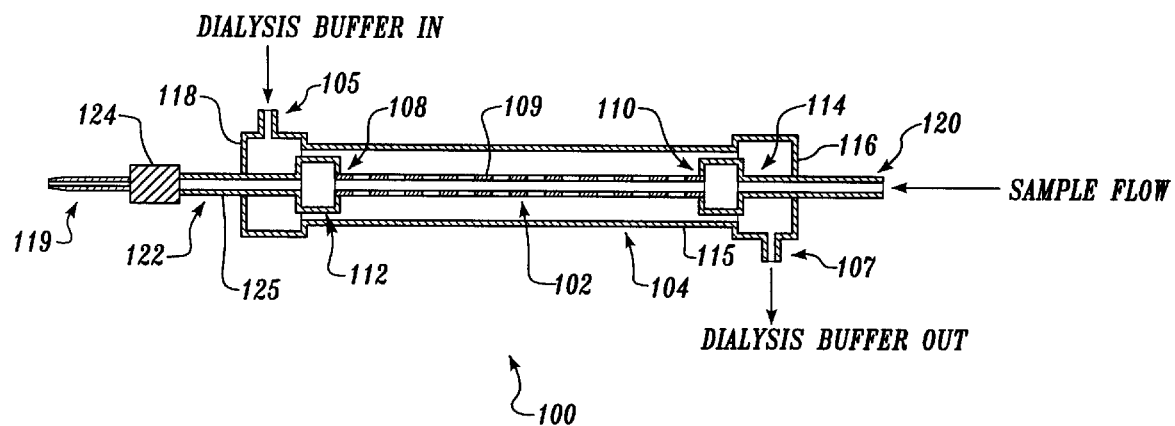
FIG. 1 is a cross section of a preferred embodiment of the microdialysis unit of the present invention.

Referring to FIG. 1, the microdialysis unit 100 has a capillary assembly 102 through which a sample flows. A shell 104 surrounds the capillary assembly 102 and forms an annular space 106 between the capillary assembly 102 and the shell 104 permitting a counter-current dialysis buffer flow, relative to sample flow inside the capillary assembly 102. The shell 104 has a buffer inlet 105 and a buffer outlet 107. The capillary assembly 102 has a dialysis tube 109 having two ends 108, 110 connected to a non-porous inlet and outlet 112, 114. The non-porous inlet and outlet 112, 114 are preferably fused silica capillary. The two ends 108, 110 of the dialysis tube 103 are inserted into the non-porous inlet and outlet 112, 114 (3 cm length) respectively and extend through and beyond the shell 104. The shell 104 may be made from an outer tube 115 attached to two low dead volume tees 116, 118 which hold both the non-porous inlet/outlet 112, 114 and the two ends of the outer tube 115.

The dialysis tube 109 is preferably a regenerated cellulose hollow fiber with a molecular weight cut-off (MWCO) less than 50,000 Da, preferably less than or equal to about of 13,000 Da for 90% retention (Spectro/Por, Part #132274, Spectrum Medical Industries, Houston, Tex.). The regenerated cellulose hollow fiber has an inside diameter less than 0.5 mm, preferably less than or equal to about 200 micrometer i.d./216 micrometer o.d., and most preferably less than 100 micrometer by any length usually from about 20 cm to about 24 cm at about 200 micrometer i.d. The outer tube 115 is preferably plastic, for example polytetrafluoroethylene (Teflon), having dimensions of about 1.59 mm o.d.×1.03 mm i.d. and any length, preferably about 30 cm.

The non-porous inlet and outlet 112, 114 are preferably fused silica capillary about 3 cm in length with an inside diameter of about 320 micrometer. Attachment to the dialysis tube ends 108, 110 is preferably with an epoxy (Loctite Co., Cleveland, Ohio).

The low dead volume tees 116, 118 are preferably stainless steel tees (Swagelok Co., Solon, Ohio).

The buffer may be any buffer compatible with the desired analysis. For ESI-MS analysis, the preferred buffer is ammonium acetate ($NH_4OAc$). The buffer concentration may range from about 0.1 mM to about 100 mM, but is preferably about 10 mM.

The sample is injected into an inlet 120 of the microdialysis unit 100 with a syringe pump (not shown) and the dialyzed sample is either directly electrosprayed through a micro-electrospray source (50 $\mu$m i.d. fused silica capillary) 119 coupled to the outlet end 122 of the microdialysis unit 100, or for off-line microdialysis, directed into a microcentrifuge tube (not shown) or other off-line sample collector for sample collection. The sample flow rate inside the dialysis tube 104 (for both on-line and off-line mode) was about 3 $\mu$L/min and may range from about 0.01 $\mu$L/min to about 25 $\mu$L/min, and the dialysis buffer flow rate was about 300 $\mu$L/min, and may range from about 50 $\mu$L/min to about 1500 $\mu$L/min.

For direct electrospray, the inlet 120 end of the microdialysis unit 100 may be connected to a syringe pump (Model 22, Harvard Apparatus, South Natick, Mass.) for sample introduction. The inlet end 120 may be a 200 $\mu$m o.d., 100 $\mu$m i.d. fused silica tubing. The outlet end 122 is coupled to the micro-electrospray source 119 (50 $\mu$m i.d) through a zero dead volume fitting system (Valco, Houston, Tex.) 124. The zero dead volume fitting 124 is connected to the non-porous outlet 112 which may include a connecting tube 125 of 200 $\mu$m o.d., 100 $\mu$m i.d. fused silica tubing. The sample solution is infused at a flow rate of 2–5 $\mu$L/min and the dialysis buffer (10 mM $NH_4OAc$) is pumped by an Applied Biosystems Solvent Delivery Module 140B (Foster City, Calif.) at a flow rate of 300 $\mu$l/min. Alternatively, the dialysis buffer may be introduced solely by gravity (i.e. vertical displacement of the buffer reservoir over the buffer outlet by ~30 cm). Although the buffer flow rate might change slightly during the dialysis process, the dialysis efficiency is not affected by variation in buffer flow rate. This eliminates the requirement for a solvent/buffer pump.

The sample may be injected through continuous infusion. Since the volume of the microdialysis tube and the associated connections is ~10 $\mu$l, 15 to 20 $\mu$l total sample volumes are consumed by continuous infusion. The sample consumption, however, is substantially reduced (>90%) by injecting only a small sample plug followed by pumping the dialysis buffer into the microdialysis system. The sample plug may be injected through an injection fitting, for example through a septum with a syringe.

For microdialysis at elevated temperature (e.g. 50° C.) or subambient temperature (0–4° C., for thermal sensitive samples or samples having limited stability after desalting), the microdialysis unit 100 may be placed inside a water bath, the temperature of which is controlled by either an external stirrer heating device or a cooling device controlling temperature to +0.5° C. The water bath is preferably stirred to ensure a homogeneous temperature inside. Any thermostatted or controlled heater would suffice to maintain the microdialysis unit 100 at an elevated temperature. An ice bath would suffice for subambient microdialysis. The elevated temperature may range from a degree above room temperature to any temperature below a sample degrading temperature, or a dialysis tube degrading temperature, whichever is lower. The subambient temperatures can range from room temperature to any temperature above the sample freezing point.

EXAMPLE 1

Reagents. Oligonucleotide #1 (5'-TGAAAGAGGAACTTGGT-3') and #2 (3'-ACTTTCTCCTTGAACCA-5') were provided by Dr. Paul Morin of University of Ontario and Ontario Cancer Institute (Toronto, ON, Canada). Oligonucleotide #3 (5'-pGCTTGCATp-3') was purchased from Biopolymer Labs, Inc. (Camden, N.J.). Oligonucleotide #4 (5'-CGACGCGGCCGCGTAATACGACTCACTATAGGGC-3') was a gift from Dr. Kwong-Kwok Wong of Pacific Northwest National Laboratory. All other reagents were obtained at the highest purity available from Sigma (St. Louis, Mo.) and used without further purification (other than the on-line microdialysis described in this work).

In this example, the microdialysis unit 100 was used on-line as described above.

Mass Spectrometry. A Finnigan TSQ 7000 triple quadrupole mass spectrometer (San Jose, Calif.) was used for the MS analysis. A sheathless micro-ESI source was constructed from a 50 $\mu$M i.d. fused silica tubing using the procedure described by Gale and Smith, Rapid Commun. Mass Spectrom. 1993, 7, 1017–1021. A coaxial SF6 sheath gas flow around the ESI emitter was used to suppress the corona discharge. For direct infusion experiments, the sample was infused at a flow rate of 0.3 $\mu$l/min. All mass spectra were obtained by signal averaging for two minutes at a scan rate of 3 sec/scan.

A potential of −2.1 kV was applied to produce a stable negative ion electrospray current. The mass spectrometer inlet capillary temperature was 140° C.

Sample preparation. All four oligonucleotide samples were diluted from stock solutions (in 10 mM $NH_4OAc$) with 10 mM $NH_4OAc$ to a final concentration of 30 $\mu$M. Another set of samples of the same concentration was prepared in 10 mM $NH_4OAc$ and 250 mM NaCl. All samples were studied using both direct infusion and the on-line microdialysis with ESI-MS. For DNA conformation studies (see Results and Discussion), oligonucleotides #1 and #2 were further diluted to a final concentration of 6 $\mu$M in 10 mM $NH_4OAc$ and 250 mM NaCl. The concentration of the dialysis buffer was varied to examine the effects of buffer concentration on both DNA duplex formation and desalting efficiency.

Although the MWCO of the dialysis tubing was claimed as 13,000 (with a retention of 90%), it was expected that the sample loss would be minimal due to the short residence time of the sample in the microdialysis tube.

Figure 2A:
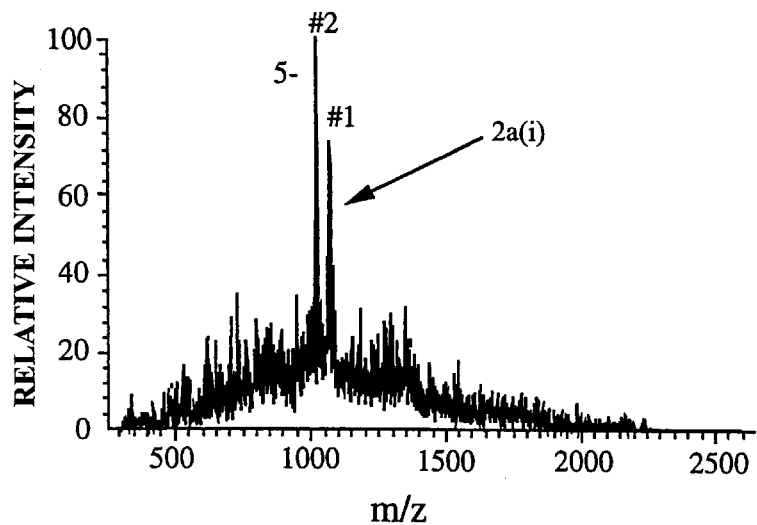
FIG. 2a is a mass spectrum of oligonucleotides #1 and #2 in 10 mM NH$_4$OAc from direct infusion.
Figure 2B:
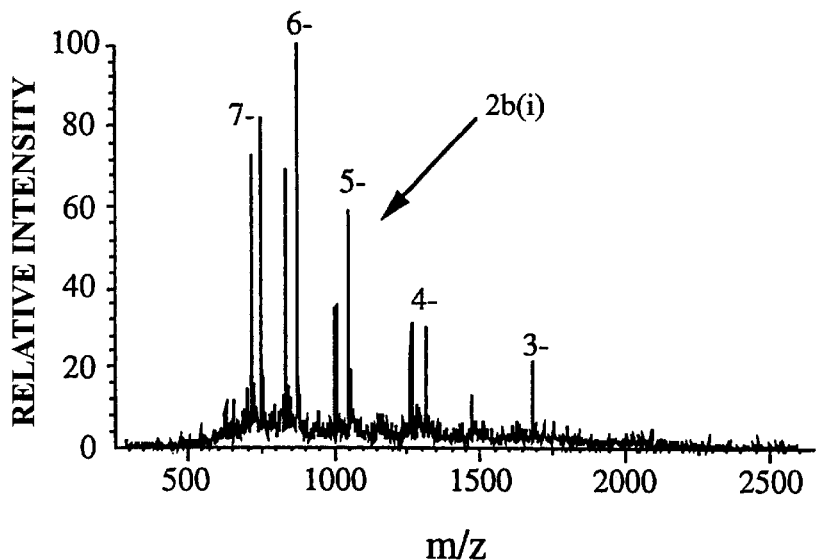
FIG. 2b is a mass spectrum of oligonucleotides #1 and #2 in 10 mM NH$_4$OAc after on-line microdialysis.
Figure 2A:
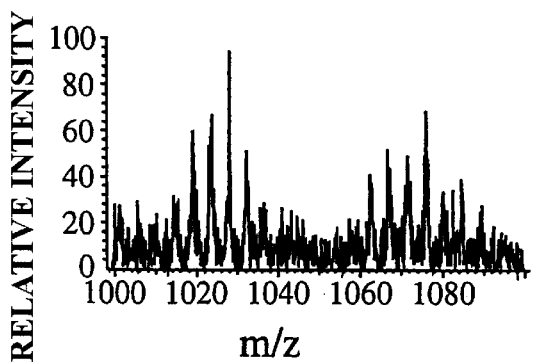
Figure 2B:
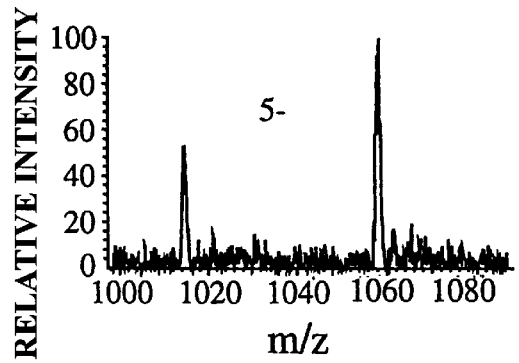

As shown in FIG. 2a, direct infusion of oligonucleotides #1 and #2 in 10 mM $NH_4OAc$ produced an uninterpretable spectrum due to sodium adduction even though the concentration of sodium was expected to be low. Only one charge state was distinctly observed for each species (FIG. 2a(I)) and the signal to noise ratio was poor. Without any cleaning or treatment step, ESI-MS clearly has only limited utility for such studies. After passing through the on-line microdialysis system, a dramatic improvement in spectrum quality was evident (FIG. 2b). The sodium adduct peaks were not observed, and a more than 5 fold increase in signal to noise ratio was obtained compared to direct infusion. Multiple charge states were also clearly observed, affording more accurate molecular weight determination for the sample components (MWcalc (#1)=5298.6 Da, MWobs (#1)= 5296.7+2.8 Da; MWcalc (#2)=5080.4 Da, MWobs (#2)= 5078.2+02.0 Da). The total time from sample injection to data acquisition was ~5 minutes.

Figure 3A:
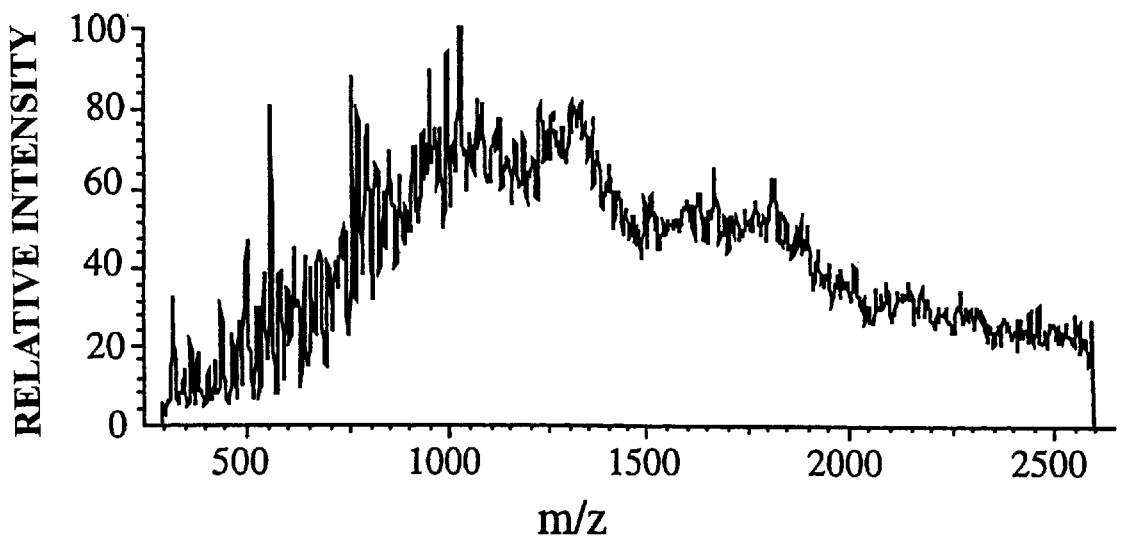
FIG. 3a is a mass spectrum of oligonucleotides #1 and #2 in 10 mM NH$_4$OAc and 250 mM NaCl by direct infusion.
Figure 3B:
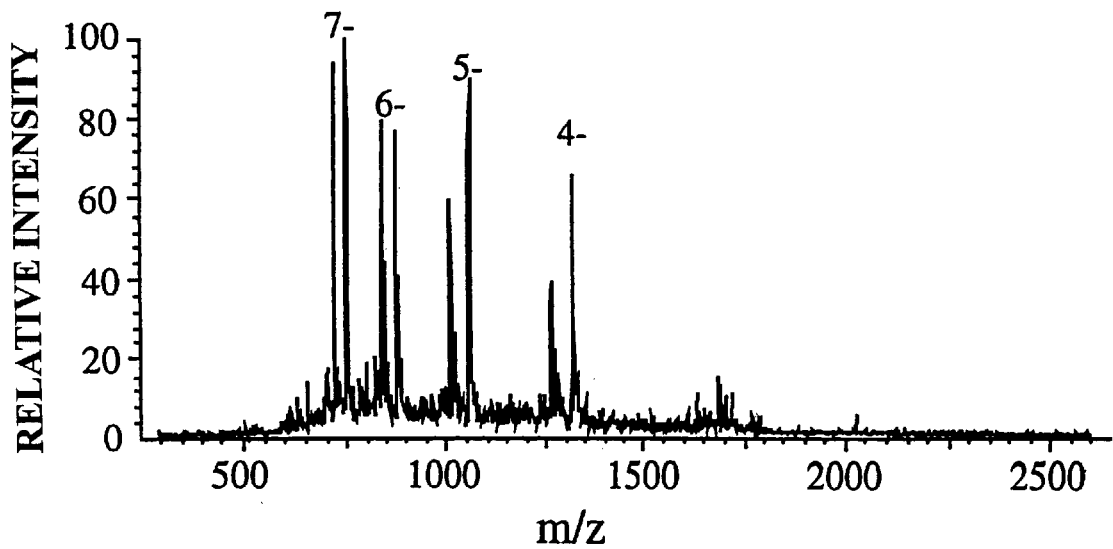
FIG. 3b is a mass spectrum of oligonucleotides #1 and #2 in 10 mM NH$_4$OAc and 250 mM NaCl after on-line microdialysis.

The microdialysis system was also evaluated at high salt concentrations (using the same sample prepared in 10 mM NH$_4$OAc and 250 mM NaCl). When analyzed by direct infusion, this sample produced a spectrum showing no analytically useful peaks (FIG. 3a). After microdialysis, an essentially identical spectrum to FIG. 2b was achieved (FIG. 3b) and the sensitivity was identical to that obtained before the addition of NaCl.

A systematic change in the flow rate of the dialysis buffer from 100 µl/min to 600 µl/min did not significantly alter the desalting efficiency. For the purpose of reducing solvent consumption and maintaining a stable dialysis buffer flow, a flow rate of 300 µl/min was used for all subsequent studies.

The sample solution flow rate was found to be important for desalting efficiency. When the sample flow rate was increased to 10 µl/min, desalting was incomplete and significant sodium adduct peaks were observed. This can be attributed to the decreased dialysis time experienced by the sample. Although a low sample flow rate would result in longer dialysis times, and therefore higher desalting efficiency, a minimum sample flow rate was found necessary to produce a stable ESI current. Since the solvent was free to cross the dialysis membrane, the effective "splitting effect" (e.g., the apparent diversion of solvent and other low molecular weight species across the microdialysis membrane) dictated that the minimum sample flow rate for a stable electrospray was higher than by direct infusion. For the experimental arrangement used in this work, 2 µl/min was found to be the minimum sample flow rate producing a stable electrospray.

The effect of the dialysis buffer concentration on desalting was also examined. An increase of dialysis buffer concentration from 10 mM to 50 mM of NH$_4$OAc did not result in any significant difference in either sensitivity or desalting efficiency.

Figure 4A:
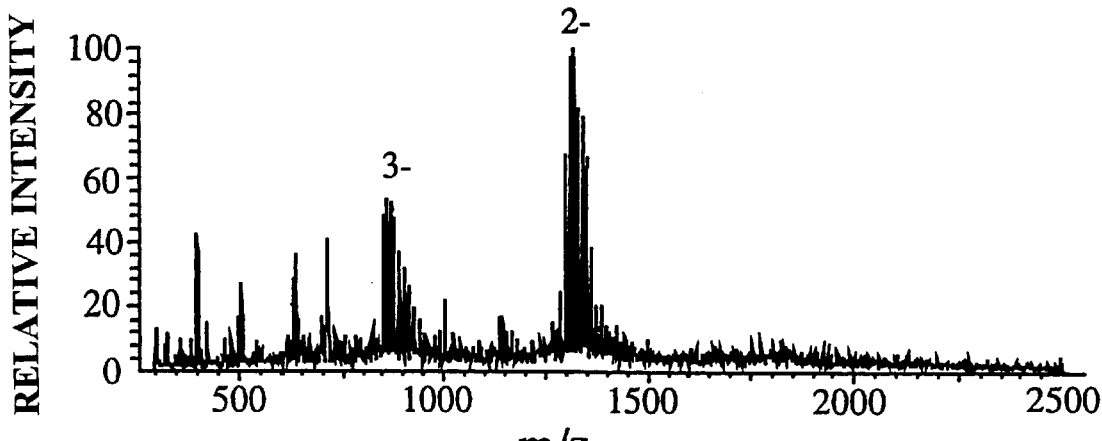
FIG. 4a is a mass spectrum of oligonucleolide #3 in 10 mM NH$_4$OAc from direct infusion.
Figure 4B:
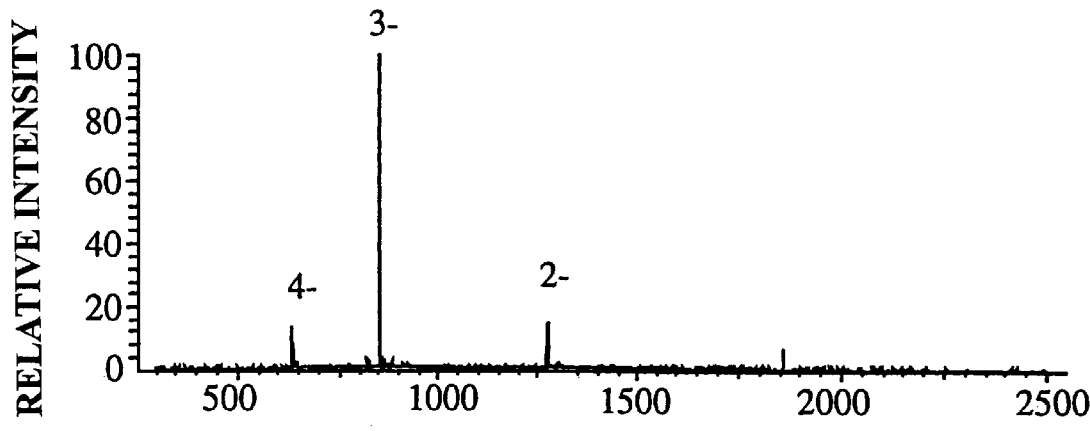
FIG. 4b is a mass spectrum of oligonucleotide #3 in 10 mM NH$_4$OAc after on-line microdialysis.
Figure 4C:
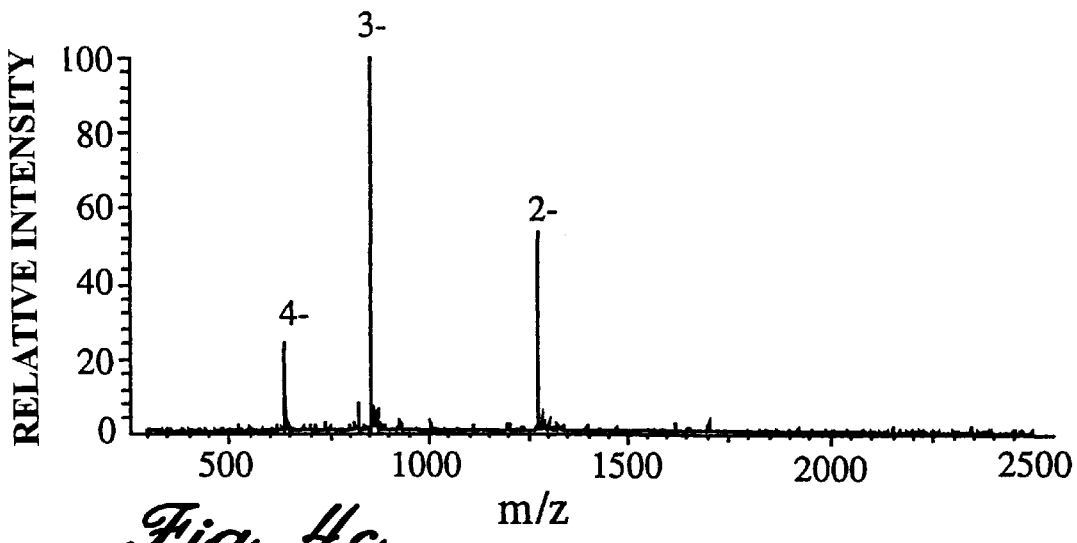
FIG. 4c is a mass spectrum of oligonucleotide #3 in 10 mM NH$_4$OAc and 250 mM NaCl after on-line microdialysis.

The effect of the size and nature of DNA samples on the desalting efficiency by on-line microdialysis. In order to further evaluate the on-line microdialysis method, oligonucleotides of different sequence and larger size were analyzed. FIGS. 4a, 4b, 4c compare mass spectra for an oligonucleotide phosphorylated at both 5'- and 3'- ends (#3) from direct infusion and on-line microdialysis. Before microdialysis, the spectrum in 10 mM NH4OAc showed up to 12 Na+ adduct ions (FIG. 4a). After microdialysis all adducts were absent (FIG. 4b) and a 10-fold increase in sensitivity was obtained. When NaCl was added to give a final concentration of 250 mM, the spectrum from direct infusion was uninterpretable (data not shown). However, a high quality spectrum, essentially identical to FIG. 4b, was obtained after the on-line microdialysis (FIG. 4c).

A 34-mer single-stranded DNA primer (#4) was used to evaluate the performance for larger oligonucleotides. For a sample concentration of ~30 µM, no useful spectrum was obtained by direct infusion (FIG. 5a). After on-line microdialysis, multiple charge states for the oligonucleotide were observed and no sodium adduction was evident (FIG. 5b). The molecular weight from the spectrum (MWobs=10, 435.8+3.0 Da) agreed well with the predicted value based on the nucleotide sequence (MWcalc=10,437.8 Da). Even at a 250 mM NaCl concentration, a useful spectrum was readily obtained (FIG. 5c). The sensitivity was only modestly affected by the addition of NaCl, indicating effective desalting was achieved by on-line microdialysis. The general observation of obtaining useful spectra from samples where direct infusion ESI-MS failed suggests that the on-line microdialysis combined with ESI-MS should be useful for the identification of minor impurities in DNA samples and the characterization of PCR products.

Figure 6:
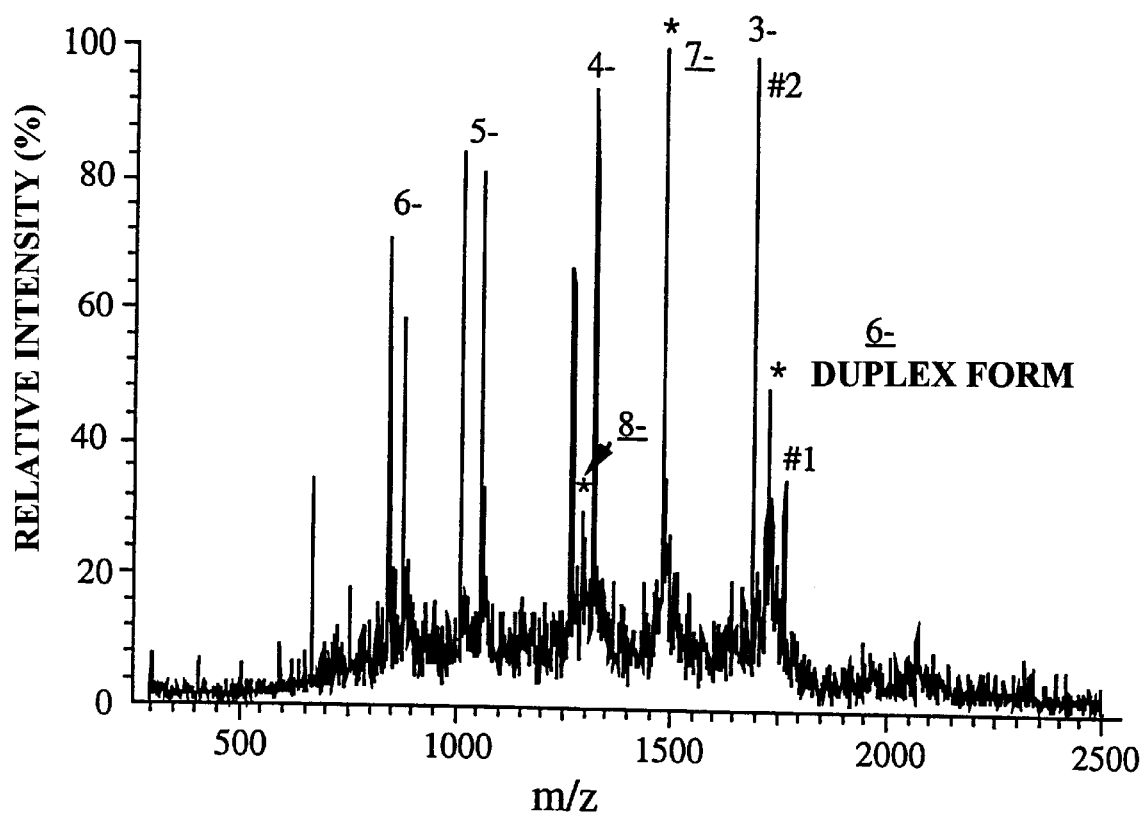
FIG. 6 is a mass spectrum of diluted oligonucleotides #1 and #2 (6 mM) in 10 mM NH$_4$OAc and 250 mM NaCl after on-line microdialysis at an inlet capillary temperature of 100° C. The three peaks labeled "*" are due to the intact double-stranded oligonucleotides.

Preservation of the duplex conformation of DNA during on-line microdialysis. Using oligonucleotides #1 and #2 as a sample, we demonstrated that the duplex association was retained during the microdialysis. At an inlet capillary temperature of 140° C., peaks corresponding to the double-stranded DNA were barely discernible in the spectrum, as shown in FIG. 2a, due to dissociation in the ESI-MS interface. When the inlet capillary temperature is reduced, peaks due to the intact duplex are expected, if present in solution. Due to sample size limitations, oligonucleotides #1 and #2 were further diluted with 10 mM NH$_4$OAc and 250 mM NaCl to a final concentration of 6 µM. Direct infusion of this sample at an inlet capillary temperature of 100° C. produced a spectrum with no analytically useful peaks because of the high concentration of salts. However, after on-line microdialysis, relatively intense peaks corresponding to the double-stranded species were observed (MWcalc= 10379.0 Da, MWobs=10378.0+1.0 Da), along with peaks due to the individual strands (FIG. 6). A dialysis buffer of 50 mM NH$_4$OAc yielded similar results.

EXAMPLE 2

Chemicals

All of the proteins and peptides used in this work were purchased from Sigma Chemical Company (St. Louis, Mo.) and were used without further purification. Ammonium acetate (Spectrum Chemical MFG Corp., Redondo Beach, Calif.) was dissolved in deionized water to a concentration of 10 mM (pH~7), and was used as the dialysis buffer, as well as to prepare the protein and peptide solutions. On-line Microdialysis and ESI-Mass Spectrometry The microdialysis unit 100 was used on-line as in Example 1.

The mass spectrometer and operating parameters were substantially the same as in Example 1. However, the electrospray ionization voltage was 2.0 to 2.3 kV. The inlet capillary temperature was 160° C. for all the samples. The reported mass spectra reported are the sum of 40 scans.

Figure 7A:
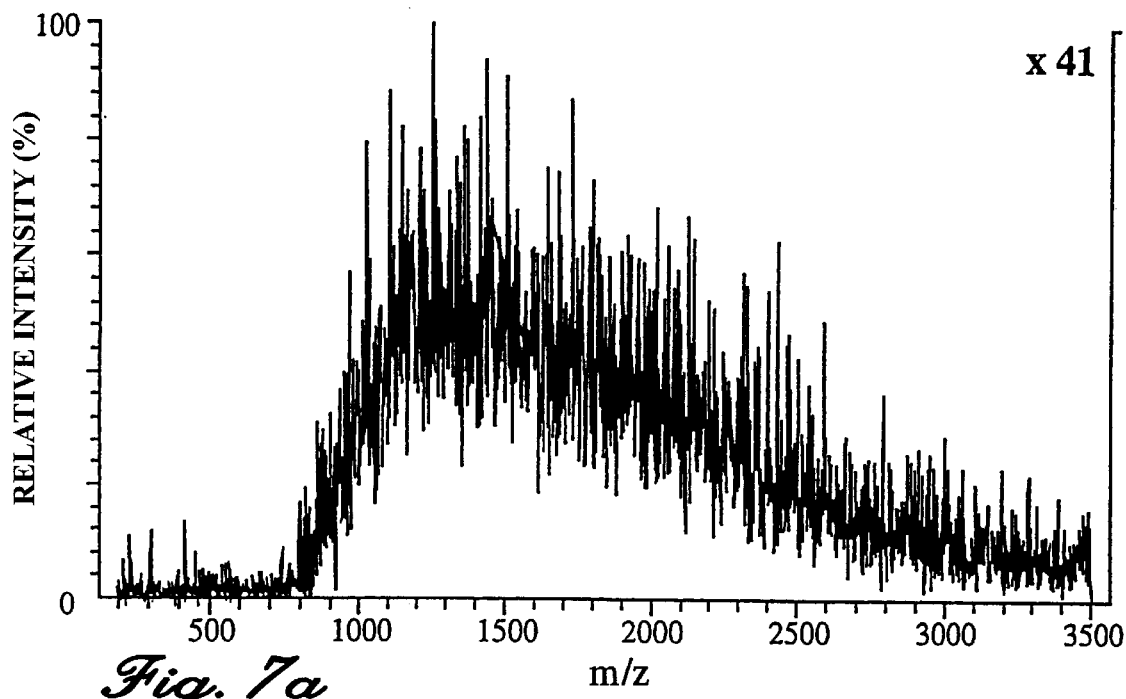
FIG. 7a is an ESI-MS spectra of apomyoglobin in 10 mM ammonium acetate and 250 mM NaCl: from direct infusion with a total protein consumption of 20 pmol.
Figure 7B:
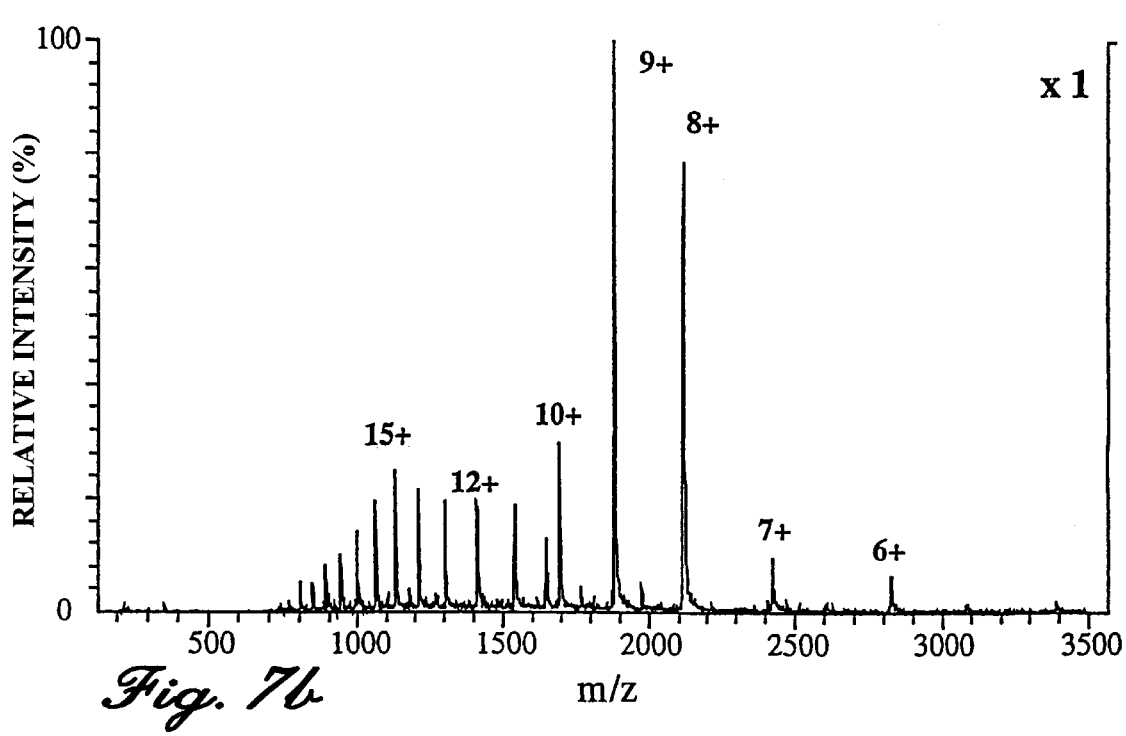
FIG. 7b is an ESI-MS spectra of apomyoglobin in 10 mM ammonium acetate and 250 mM NaCl: after on-line desalting with a total protein consumption of 12 pmol, and a signal-to-noise ratio increased by a factor of more than 40 after desalting.

FIG. 7a shows a typical spectrum of horse apomyoglobin (MW 16,951 Da) at a concentration of 36 mM in 10 mM ammonium acetate and 250 mM NaCl, obtained by direct infusion with the micro-ESI source. Due to the extensive sodium adduction, charge states for the molecular ions were not resolved and signal to noise ratio of the spectrum was poor. Under these conditions, similar poor results were also obtained for other proteins, including ubiquitin, carbonic anhydrase and albumin. However, when the apomyoglobin solution (1.2 µM) was injected through the on-line microdialysis of the present invention to the ESI source at a flow rate of 5 µL/min with the same solvent and salt concentration as above (using a dialysis buffer flow rate of 300 µl/min) and electrosprayed under otherwise identical conditions, the spectrum shown in FIG. 7b was obtained. The actual desalting time was ~1.5 min, i.e., the time the sample spent inside the micro-dialysis tube. No sodium adducts were evident and the signal-to-noise ratio was >40 times greater that for the spectrum shown in FIG. 7a. The total protein consumption was calculated to be 20 pmol and 12 pmol for the mass spectra in FIGS. 7a and 7b, respectively.

With the present on-line design, effectively complete desalting was achieved at sample infusion rates in the range of 2–5 µL/min. In other words, the amount of residual salt, if any, was below detection limits of the ESI-MS. Although the flow rate at the ESI emitter was greater than typically used for micro-electrospray, the source was stable in operation. It was possible to obtain a mass spectra clearly displaying peaks for several charge states of apomyoglobin at a solution concentration of ~0.012 μM in a 250 mM NaCl buffer (total consumption was 120 fmol).

Desalting experiments have also been performed for the apomyoglobin solution using buffer flow rates of 100 to 800 μl/min. A flow rate of 300 μl/min was found to give best results and was used for subsequent experiments, although high quality mass spectra were obtained for buffer flow rates between ~300 and ~500 μl/min. An insufficient buffer flow rate would not remove the salts fast enough.

Although the specified molecular weight cut-off for the dialysis tube was 13,000 Da, the effective mass limit for our device as used was much lower. For example, we have successfully desalted angiotensin I (1296 Da) in a solution containing 10 mM ammonium acetate and 250 mM NaCl. Up to six sodium ions were observed attaching to a 2+ charge state ion of angiotensin I in the presence of 250 mM NaCl, whereas no sodium adducts were detected after on-line microdialysis desalting. Experimental conditions, including buffer concentration and flow rate, were the same as those for apomyoglobin. The success for analysis of these small molecules was probably due to the limited dialysis time and the relatively slow kinetics (compared with ammonium acetate) for diffusion out of the dialysis tube. Based upon these results, desalting of smaller molecules should also be possible using dialysis tubes of lower molecular weight cut-off.

Figure 8A:
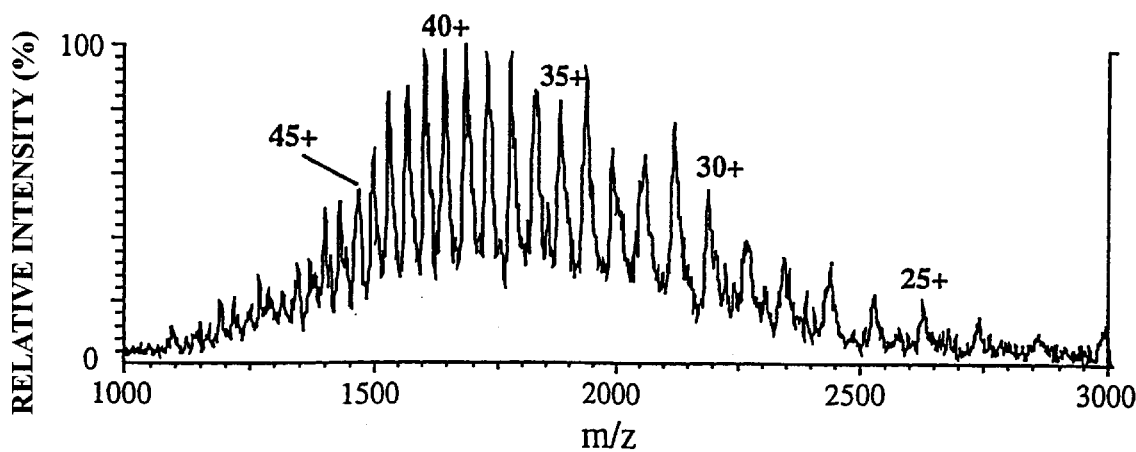
FIG. 8a is an electrospray mass spectra of bovine albumin (8 $\mu$M in 10 mM NH4OAc): from direct infusion, giving a deconvoluted molecular weights calculated from the spectra of 65,645±200 Da.
Figure 8B:
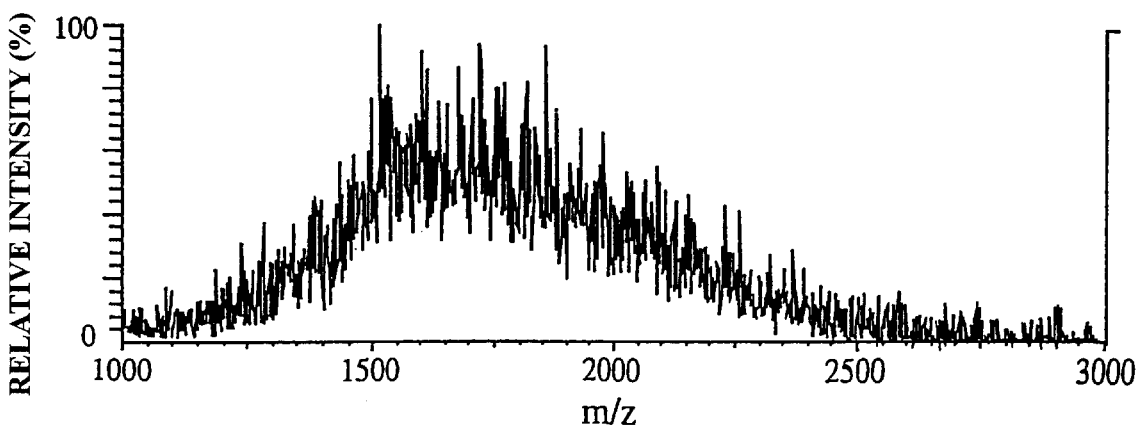
FIG. 8b is an electrospray mass spectra of bovine albumin (8 $\mu$M in 10 mM NH4OAc): from direct infusion with 250 mM NaCl.
Figure 8C:
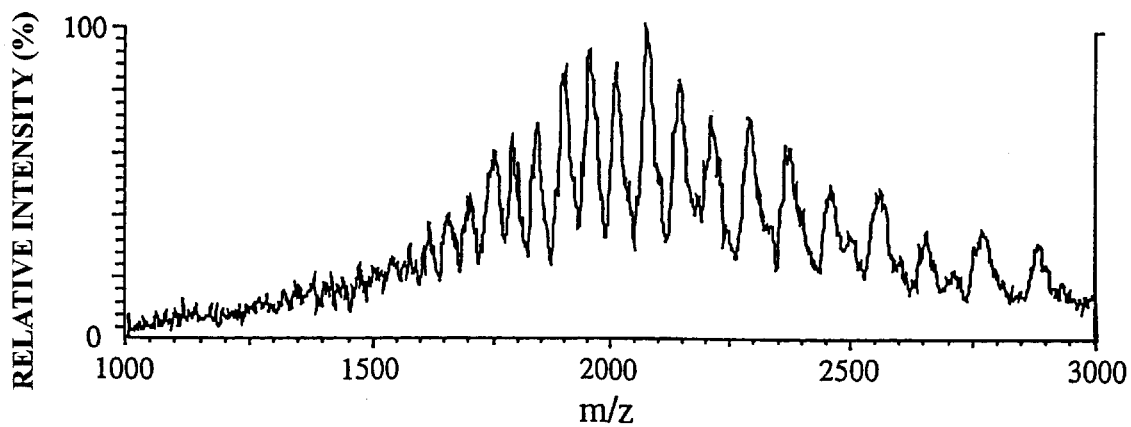
FIG. 8c is an electrospray mass spectra of bovine albumin (8 $\mu$M in 10 mM NH4OAc): from the same solution as for FIG. 8b, but after on-line desalting at a sample flow rate of 5 ml/min, giving a deconvoluted molecular weights calculated from the spectra of 65,640±200 Da.
Figure 8D:
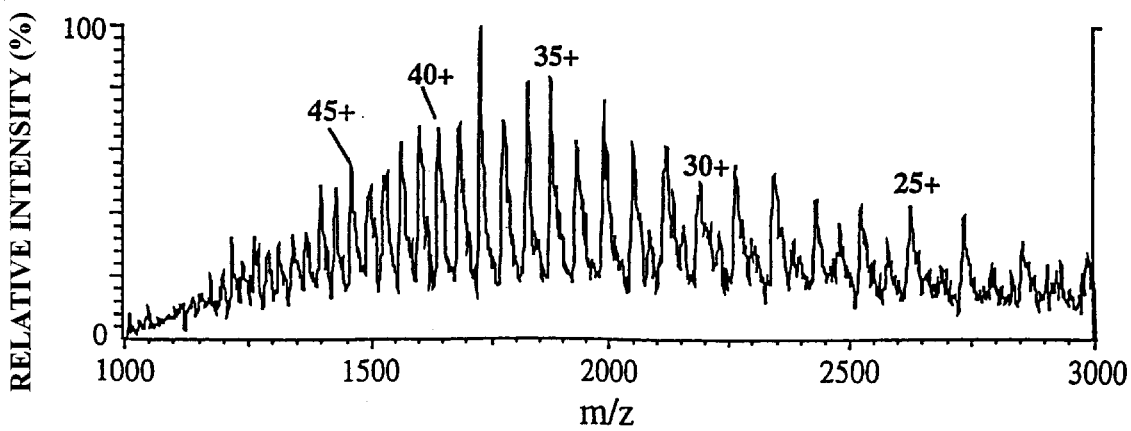
FIG. 8d is an electrospray mass spectra of bovine albumin (8 $\mu$M in 10 mM NH4OAc): same conditions as for FIG. 8c, except with a sample flow rate of 2 $\mu$L/min, giving a deconvoluted molecular weights calculated from the spectra of 65,640±200 Da.

A typical ESI spectrum of horse serum albumin is shown in FIG. 8a, which gives a molecular weight of 65,645+200 Da. The sample was dissolved in 10 mM ammonium acetate to a concentration of 8 μM. Upon the addition of 250 mM NaCl, no peaks corresponding to the various charge states of the protein could be identified in the ESI mass spectrum (FIG. 8b). When the same sample was electrosprayed using the on-line desalting method at a sample infusion rate of ~5 μl/min (corresponding to ~1.5 minutes of desalting), charge state distribution was clearly resolved, as shown in FIG. 8c. Interestingly, deconvolution of the spectrum yielded a molecular weight of 66,420+500 Da, which is higher than obtained for the pure sample. This mass difference likely arises from incomplete desalting for this protein. This was confirmed by a molecular weight of 65,640+200 Da obtained from FIG. 8d when the sample infusion rate was reduced to 2 μl/min (i.e., by providing a longer desalting time of ~3.5 minutes). These results show that the effectiveness of desalting is also dependent upon the nature of the salt interaction with the biopolymers and their intrinsic exchange rates in solution. In the case of the albumin, some of the sodium ions may occupy internal sites of the protein that would presumably be exchanged at inherently slower rates, in a similar fashion as in H/D exchange with $D_2O$.

EXAMPLE 3

An experiment was conduction to compare the method of the present invention with current desalting methods.

Materials

A polydeoxynucleotide d(pT)18 was purchased from Sigma (St. Louis, Mo., USA). All other reagents of analytical grade or better were purchased from Sigma and used as received.

Methods

The on-line microdialysis system was the same as in Examples 1 and 2.

Sample preparation. 60 μM d(pT)18 was prepared in 10 mM $NH_4OAc$ and 100 mM NaCl. The oligonucleotide samples containing organic bases were prepared using the above oligonucleotide samples and stock solutions of 100 mM piperidine and 100 mM imidazole to a final concentration of 25 mM of each base. For multiple buffer exchange experiments, 50 μL of 60 μM d(pT)18 in 10 mM $NH_4OAc$ and 100 mM NaCl was diluted with 10 mM $NH_4OAc$ to 500 μL in a Centricon-3 (Amicon, Beverly, Mass.) membrane cartridge and the final solution was centrifuged at 7000 rpm (4000 rcf units) for 45 minutes. The retentate was further diluted with the same buffer and centrifuged. This process was repeated four more times and the final retentate (~50 μL) was collected for MS analysis. Mass spectrometry The mass spectrometer and operating parameters were the same as for Example 2.

Figure 9A:
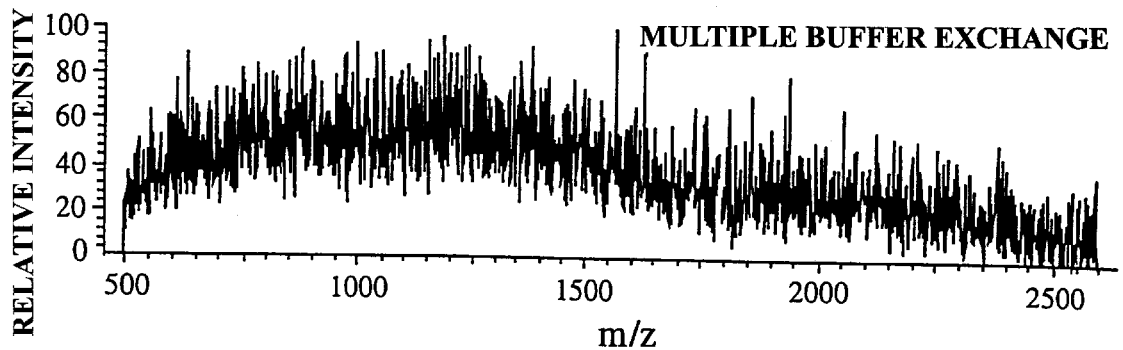
FIG. 9a is a spectrum obtained after 5 cycles of buffer exchange against 10 mM NH4OAc using a Centricon-3 membrane cartridge.
Figure 9B:
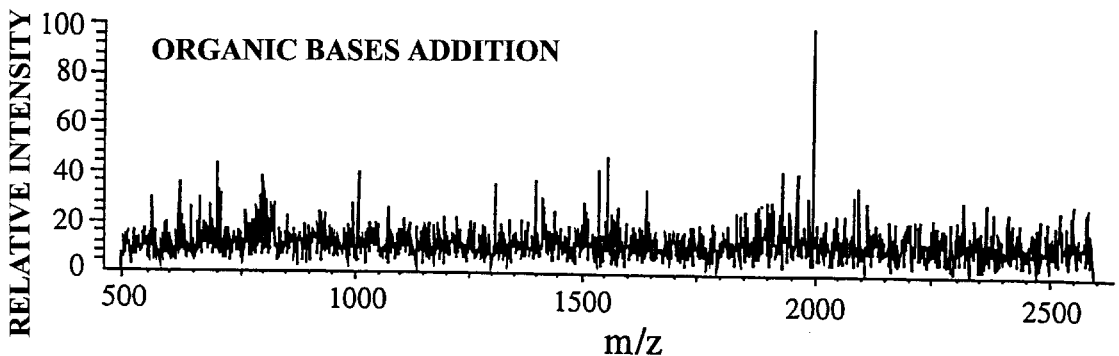
FIG. 9b is a mass spectrum obtained after addition of piperidine and imidazole into the sample (25 mM final concentration of each base).
Figure 9C:
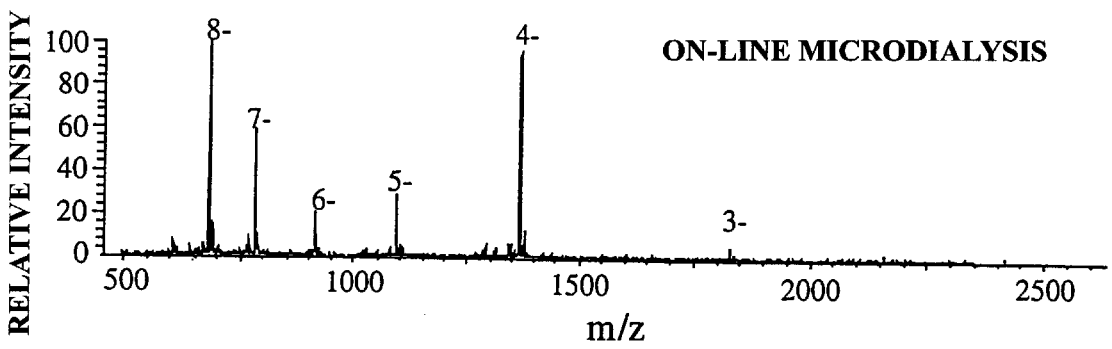
FIG. 9c is a mass spectrum obtained after on-line microdialysis against 10 mM NH4OAc.

In order to further demonstrate the superiority of microdialysis over the other desalting techniques, a sample containing 60 μM d(pT)18 in 10 mM NH4OAc and 100 mM NaCl was desalted by three different techniques (multiple buffer exchange, organic bases addition and on-line microdialysis) followed by ESI-MS analysis. A dramatic difference in desalting efficiency and subsequent mass spectrum quality was observed. FIG. 9a shows the mass spectrum of 60 μM d(pT)18 in 10 mM $NH_4OAc$ and 100 mM NaCl after 5 cycles of buffer exchange (~4 hours) against 10 mM $NH_4OAc$. No analytically useful signal was observed, which could be attributed to the combining effects of sample loss and incomplete desalting. When piperidine and imidazole (25 mM each) were added to the original sample and the sample analyzed by ESI-MS, greatly suppressed background signal and some minor peaks were observed (FIG. 9b), but the detection sensitivity and the signal to noise ratio (S/N) were low and an accurate mass measurement was not obtainable. Note that after on-line microdialysis of the same original sample, sodium adducts were completely removed from the mass spectrum and peaks corresponding to different charge states were observed in high abundance (FIG. 9c). An accurate mass molecular weight measurement was readily obtained, allowing for further structural studies to be conducted.

From the data presented in FIG.'S 9a, 9b, and 9c and other significant experiments (data not shown), the on-line microdialysis approach is demonstrated to offer several distinct advantages. First, the total analysis time for obtaining a good quality spectrum in on-line microdialysis is ~5 minutes. Thus, the desalting speed of microdialysis is comparable to organic bases addition method and over an order of magnitude faster than multiple buffer exchange and precipitation techniques. Second, the salt concentration tolerance in on-line microdialysis (1.3 M NaCl for proteins and 0.5 M NaCl for oligonucleotides using the current microdialysis design) is at least an order of magnitude higher than the other methods. For multiple buffer exchanges, a higher salt concentration may be compensated by additional dilution and concentration cycles, but longer desalting time and more sample losses are unavoidable. Third, the sample volume requirement for on-line microdialysis (~15–20 μL) is comparable to that of organic bases addition method, but much smaller than that for multiple buffer exchange and precipitation methods.

EXAMPLE 4

An experiment was conducted to demonstrate off-line microdialysis.

Materials

A polydeoxynucleotide d(pT)18 was purchased from Sigma (St. Louis, Mo., USA). A sample containing two complimentary single-stranded 17-mer oligonucleotides (Strand A. 5'-TGAAAGAGGAACTTGGT-3'; Strand B. 3'-ACTTTCTCCTTGAACCA-5') was a gift from Dr. Paul Morin of University of Ontario and Ontario Cancer Institute (Toronto, ON, Canada). All other reagents of analytical grade or better were purchased from Sigma and used as received.

Sample Preparation.

The following samples were prepared: 1) 10 mM apomyoglobin in 10 mM NH$_4$OAc and 1.5 M NaCl; 2) 3 µM 17-mer oligonucleotides in 10 mM NH$_4$OAc and 150 mM NaCl; and 3) 60 µM d(pT)18 in 10 mM NH$_4$OAc and 100 mM NaCl. The oligonucleotide samples containing organic bases were prepared using the above oligonucleotide samples and stock solutions of 100 mM piperidine and 100 mM imidazole with a final concentration of 25 mM of each base. The on-line microdialysis system was the same as in Examples 1 and 2. For on-line microdialysis performed at elevated temperature, the microdialysis unit was placed in a stirred bath heater (1.7-L) controlled to a temperature of 50° C.+0.5° C. For off-line microdialysis, the micro-electrospray source was replaced with a microcentrifuge tube for sample collection.

While on-line microdialysis has been shown to be rapid and effective, a major limitation with the on-line approach is the relatively high sample flow rate requirement. A minimum sample flow rate of ~2 µL/min was required to obtain a stable ESI current due to the solvent diversion across the dialysis membrane as discussed previously. This flow rate is about 10 times and 100 times higher than that used for microspray (0.1–0.3 µL/min) and "nanospray" (20–40 nL/min), respectively.

Figure 10A:
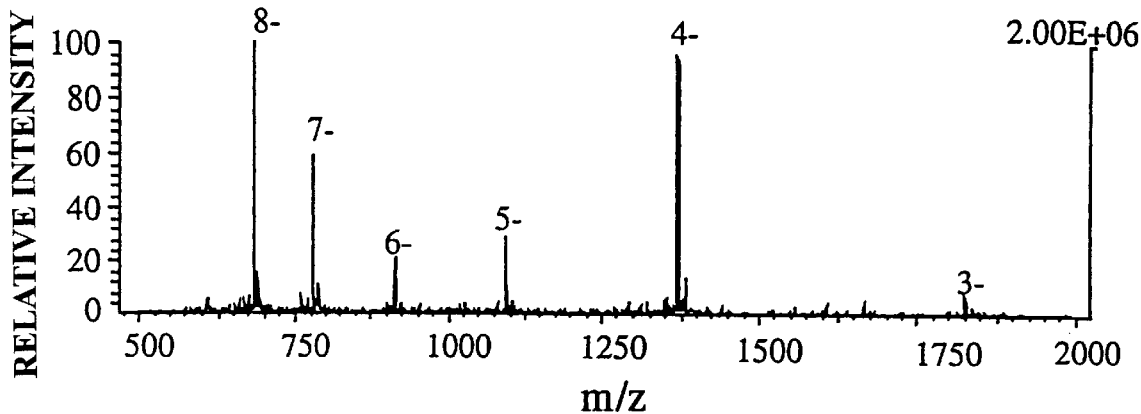
FIG. 10a is a mass spectrum of 60 $\mu$M d(pT)18 in 10 mM NH4OAc and 100 mM NaCl was obtained after on-line microdialysis against 10 mM NH4OAc, consuming a sample of 360 pmoles.
Figure 10B:
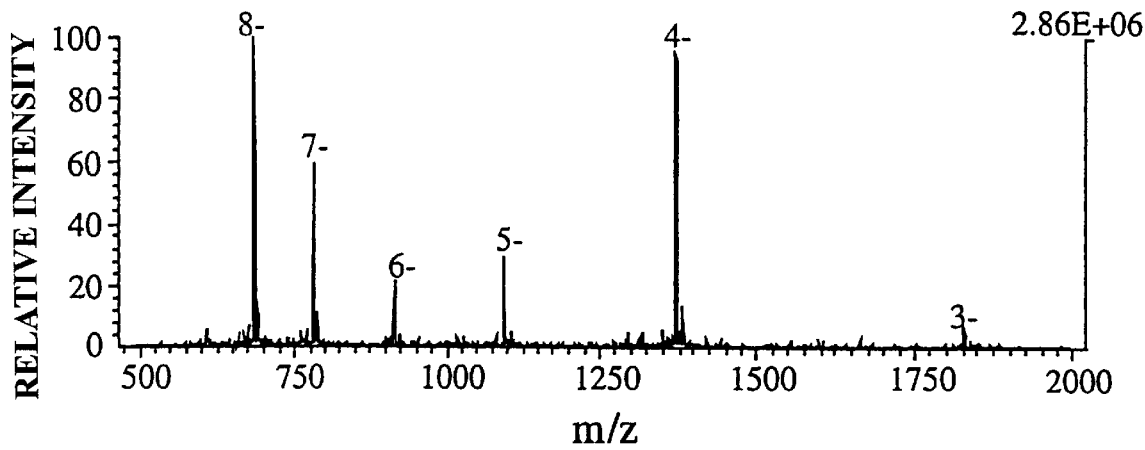
FIG. 10b is a mass spectrum of 60 $\mu$M d(pT)18 in 10 mM NH4OAc and 100 mM NaCl was obtained from direct infusion micro-electrospray after off-line microdialysis against 10 mM NH4OAc, consuming a sample of 36 pmoles.

In order to circumvent this limitation, we modified the on-line system to off-line sample cleanup by replacing the micro-electrosprayer with a microcentrifuge tube for sample collection. This design will preserve the fast and efficient desalting offered by microdialysis, as well as allow the analysis of the dialyzed sample by micro-electrospray or nano-electrospray, greatly reducing the sample consumption. FIGS. 10a and 10b is compared to the mass spectra of the same d(pT)18 sample as shown in FIG. 9c after on-line and off-line microdialysis. As expected, no significant difference was found between the two spectra. Note that, however, the sample consumed in FIG. 10a was 360 pmoles, while that in FIG. 10b was only 36 pmoles. Based on the signal intensities in FIGS. 10a and 10b, it can be concluded that a 14-fold decrease in sample consumption was achieved by using off-line microdialysis followed with microspray ESI-MS analysis for obtaining a similar quality spectrum. It is important to note that we did not attempt to determine detection limits in this comparison, and it is obvious that useful spectra are obtainable from much smaller sample sizes than used here.

Another advantage of off-line scheme, as we have experienced in recent studies, is that much lower sample flow rates (0.3 µL/min to 1.0 µL/min) can be used if longer dialysis time is needed for desalting of samples with complicated matrices (a typical example of such a matrix contains: 0.1 M Tris/HCl, 0.5 M NaCl, 10% glycerol and 1–2 mM of DTT and other preservatives often added to biological samples). Although lower sample flow rates did not generate a stable ESI current in the on-line mode with our present ESI source, samples can be cleaned up using the dialysis system. Indeed, nearly quantitative recoveries have been achieved when 10 µL of 30 µM apomyoglobin was dialyzed at a sample flow rate of 0.5 µL/min (using a BCA protein assay method). Currently, ESI-MS analysis of ~10 µL of protein or DNA sample in complicated matrix resorting to off-line microdialysis desalting has been routinely successful in our laboratory. Research involving small sample volumes had been extremely difficult, if not impossible, before the introduction of microdialysis. We anticipate that, complementary to the on-line microdialysis scheme, the flexibility of off-line approach will further extend the applicability of microdialysis in ESI-MS and other related studies involving biopolymers.

Figure 11A:
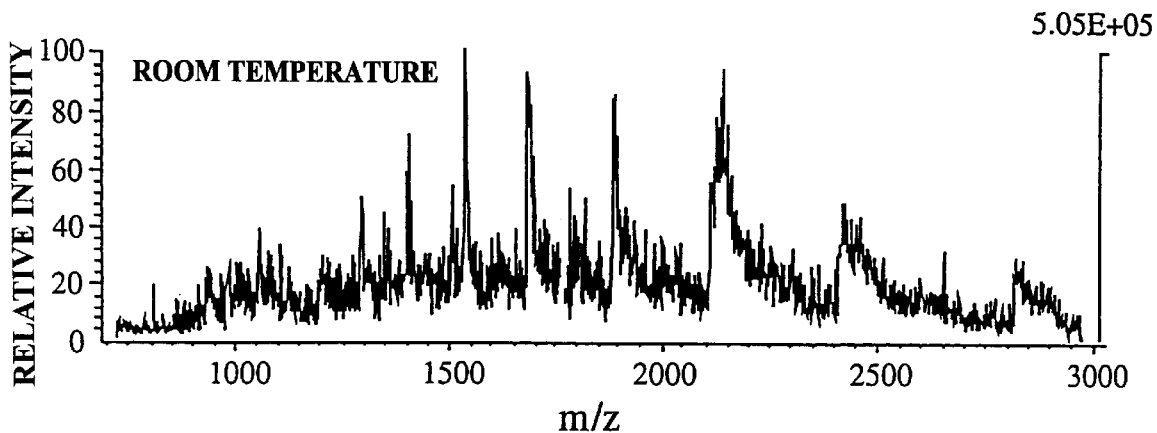
FIG. 11a is a mass spectrum of 10 $\mu$M apomyoglobin in 10 mM NH4OAc and 1.5 M NaCl obtained after on-line microdialysis at room temperature.
Figure 11B:
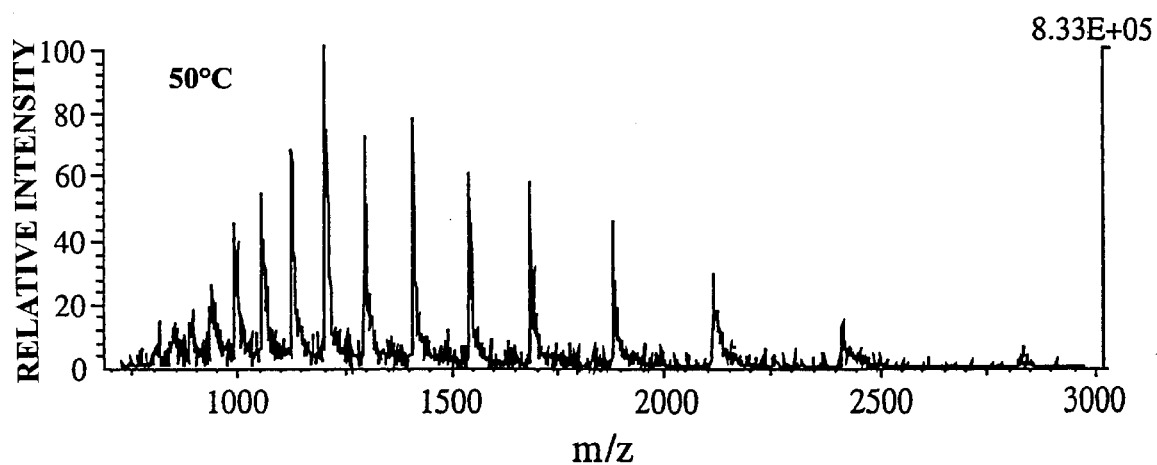
FIG. 11b is a mass spectrum of 10 mM apomyoglobin in 10 mM NH4OAc and 1.5 M NaCl obtained after on-line microdialysis at 50° C.

Higher temperature greatly increases the dialysis efficiency and improves the spectrum quality. Since dialysis is a diffusion-controlled process, an increase in dialysis temperature is expected to further increase the diffusion rates of salt components (relative to large biopolymers), resulting in a higher dialysis efficiency. An additional advantage of higher temperatures is that small ions more closely associated with biopolymers in solution (i.e., "condensed" counter ions) will also be less strongly associated, allowing more rapid exchange and removal. FIGS. 11a and 11b compares the mass spectra of 10 mM apomyoglobin in 1.5 M NaCl after on-line microdialysis at room temperature (FIG. 11a) and at 50° C. (FIG. 11b). At room temperature, even with the efficient desalting provided by microdialysis, the spectrum showed only a few charge states with low sensitivity, and significant sodium adduction was evident (FIG. 11a). When the microdialysis was performed at 50° C., the spectrum quality was greatly improved (FIG. 11b). Multiple (and higher) charge states were observed with high abundance and sodium adduction was minimal (FIG. 11b). An accurate molecular weight was determined despite the presence of some residual sodium adduction, with at least a 5-fold increase in S/N. When the highest tolerable NaCl concentration (which we arbitrarily define as that producing a spectrum with the most intense peaks arise from intact molecular ions) was used to assess the dialysis efficiency, this concentration was increased from 1.3 M at room temperature to 2 M at 50° C. When the NaCl concentration was further increased to 2.67 M, a similar spectrum to that in FIG. 11b was obtained with the major molecular ions corresponding to intact molecule with only one sodium attached (data not shown), and an accurate molecular weight was still readily determined. This indicated that a higher dialysis temperature should be advantageous for addressing more complex and impure samples providing that the biopolymers are stable (e.g., do not aggregate, etc.) at the elevated temperature. (Note that the suggested maximum operating temperature for the microdialysis fiber is 60° C.).

Figure 12A:
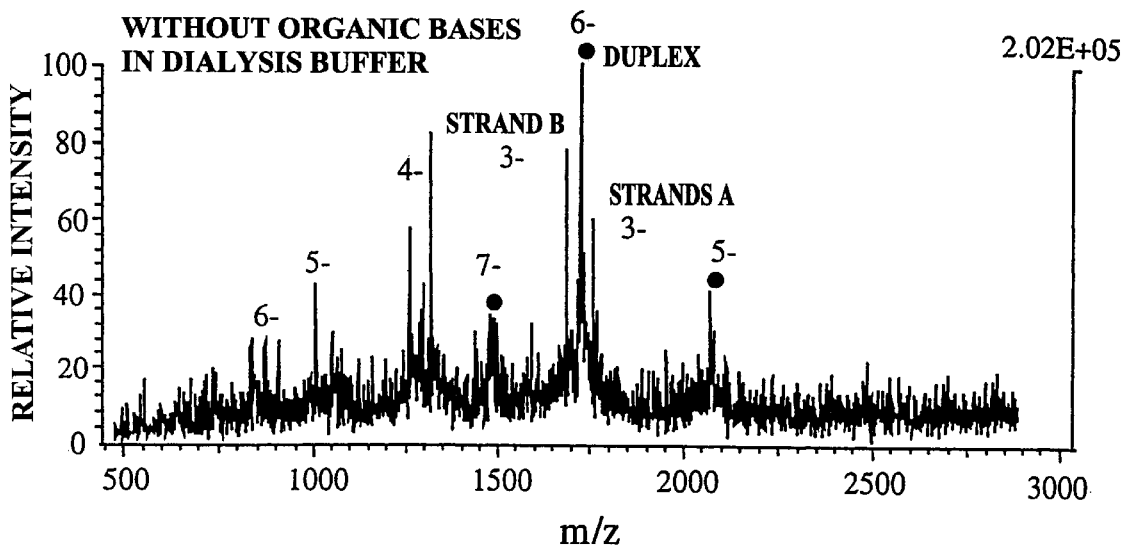
FIG. 12a is a mass spectrum of 17-mer oligonucleotides in 10 mM NH4OAc and 150 mM NaCl was obtained after on-line microdialysis using 10 mM NH4OAc as dialysis buffer wherein peaks labeled "o" arises from double-stranded DNA.
Figure 12B:
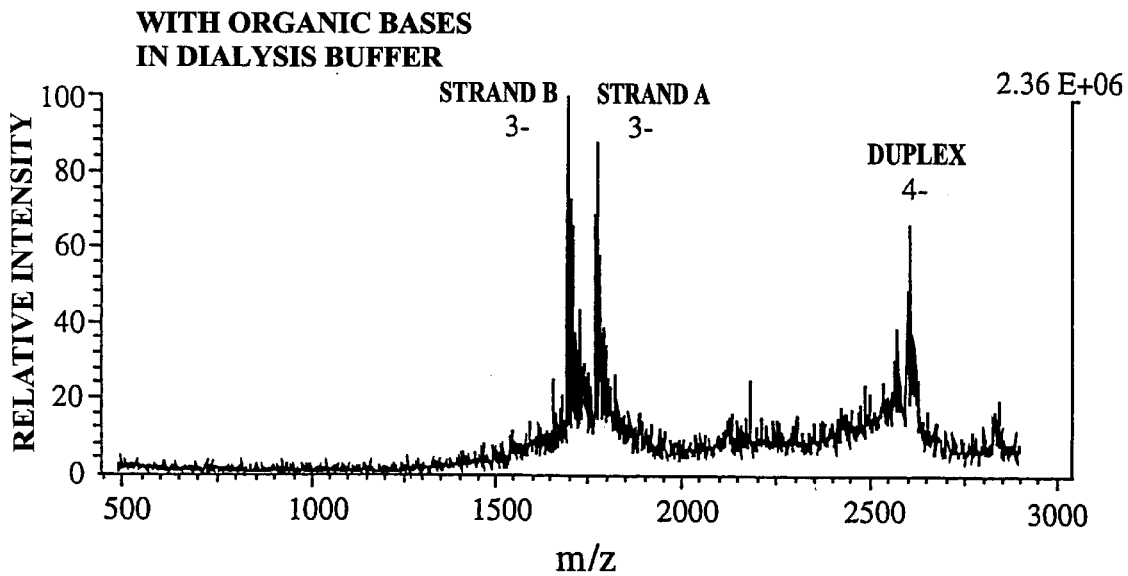
FIG. 12b is a mass spectrum of 17-mer oligonucleotides in 10 mM NH4OAc and 150 mM NaCl was obtained after on-line microdialysis using 10 mM NH4OAc, 25 mM piperidine and 25 mM imidazole as dialysis buffer exhibiting a charge state reduction and sensitivity enhancement.

Addition of organic bases in dialysis buffer reduces charge states and further increases detection sensitivity for oligonucleotides samples. A large number of inorganic or organic additives (or modifiers) have been widely used in ESI-MS for sensitivity enhancement. While essentially an infinite number of composition and concentration of additives could be investigated, several have been shown to be effective in most cases studied. In particular, Greig and Griffey, and Muddiman et al reported that the addition of piperidine and imidazole in DNA samples has been shown to significantly suppress sodium adduct ions and improve S/N.[20,21] Muddiman et al have also studied the charge state reduction of oligonucleotide negative ions by imidazole for sensitivity enhancement [21]. As a model system to investigate the potential advantages of combining additives with microdialysis, piperidine and imidazole were added to the dialysis buffer (i.e. 10 mM NH4OAc and 25 mM of each base) for DNA sample desalting. A sample consisting of two complimentary 17-mer oligonucleotides (see Materials for sequences) were analyzed by on-line microdialysis. A low inlet capillary temperature (120° C.) was used to facilitate the detection of double-stranded (duplex) oligonucleotides. FIG. 12a shows the mass spectrum obtained using 10 mM NH4OAc as the dialysis buffer. Charge states corresponding to both the individual strands and the duplex form were observed. Within the S/N limit of this data, no sodium adduction was apparent. After addition of piperidine and imidazole into the dialysis buffer, a much simpler spectrum was obtained (FIG. 12b). Interestingly, only one charge state was observed for both the individual strands and the duplex form along with a shift to higher m/z (lower charging). A 5-fold increase in S/N compared to the signal in FIG. 12a was also achieved. These results demonstrated a further increase in sensitivity due to the addition of piperidine and imidazole in the dialysis buffer. It is expected, therefore, other additives can also be incorporated in the dialysis buffer to improve ESI-MS analysis for specific analytes.

Figure 13A:
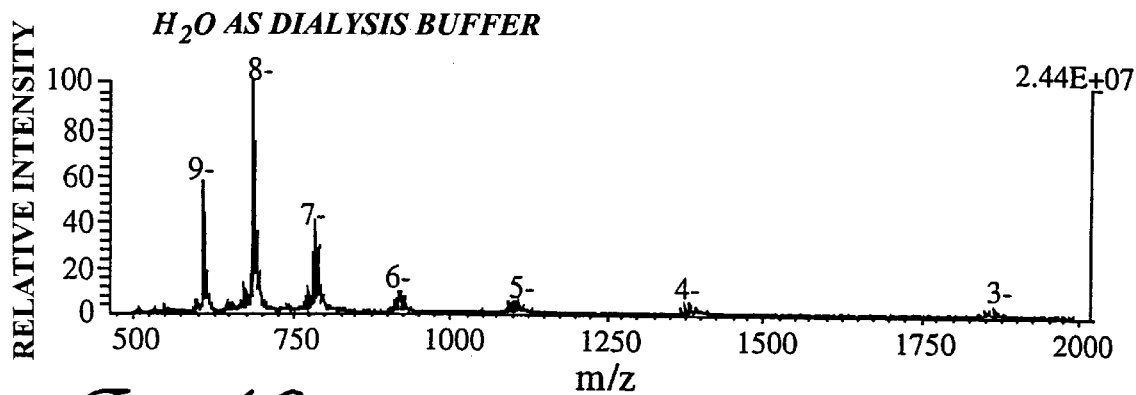
FIG. 13a is a mass spectrum of 60 $\mu$M d(pT)18 in 10 mM NH4OAc and 100 mM NaCl obtained after on-line microdialysis using H2O as dialysis buffer.
Figure 13B:
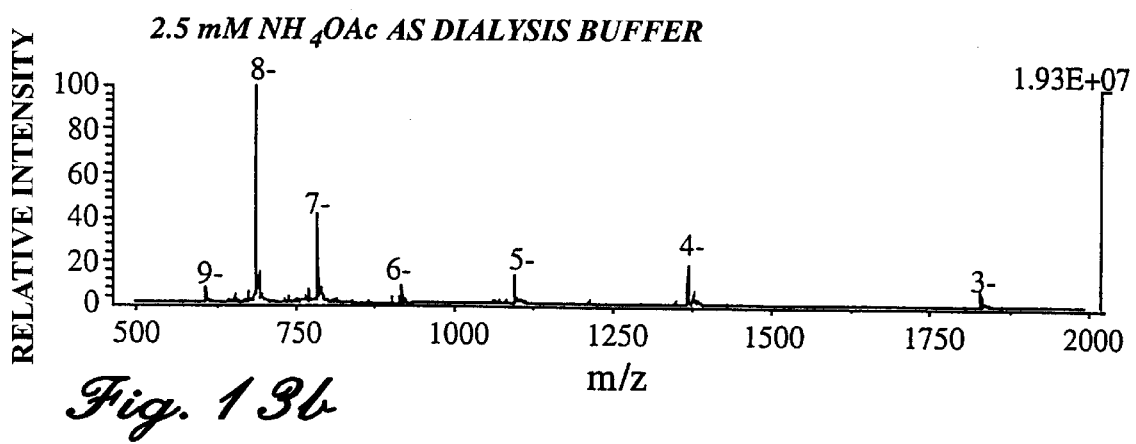
FIG. 13b is a mass spectrum of 60 $\mu$M d(pT)18 in 10 mM NH4OAc and 100 mM NaCl obtained after on-line microdialysis using 2.5 mM NH4OAc as dialysis buffer.
Figure 13C:
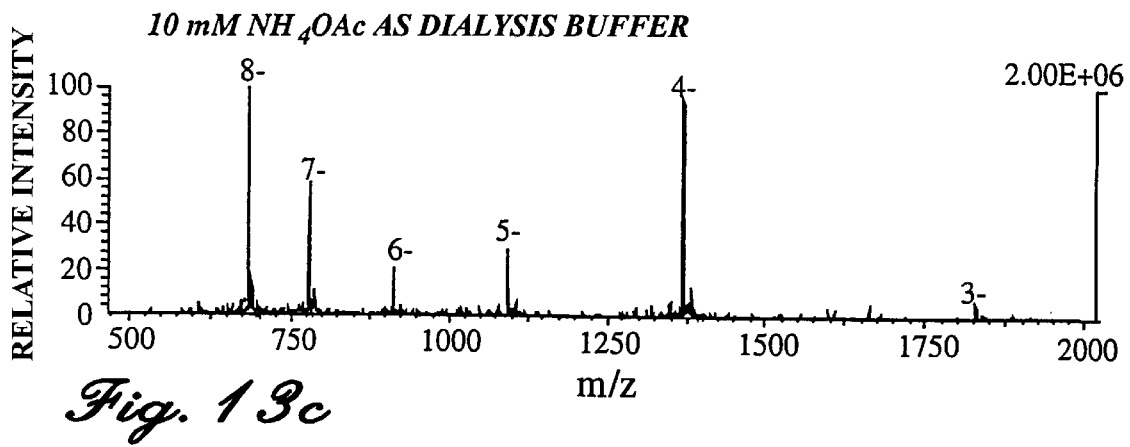
FIG. 13c is a mass spectrum of 60 $\mu$M d(pT)18 in 10 mM NH4OAc and 100 mM NaCl obtained after on-line microdialysis using 10 mM NH4OAc as dialysis buffer.

Use of low concentration (0–2.5 mM NH4OAc) dialysis buffer shifts the DNA negative ions to higher charge states, and results in a 10-fold increased in detection sensitivity and a slightly decreased desalting efficiency. Previous experience has indicated that DNA samples, when dissolved in <5 mM $NH_4OAc$ and analyzed by ESI-MS, produced molecular negative ions with higher charge states and more sodium adduction than samples dissolved in >10 mM $NH_4OAc$. Since the sodium adduction arose from the salt contamination, the use of microdialysis is expected to eliminate or significantly reduce sodium adduction. The shift of molecular ions to higher charge states suggests that low concentrations of buffer should favor DNA analysis: the lower m/z values will extend the size of DNA molecules amenable to MS, and an increase in sensitivity is expected due to the more efficient detection of mass spectrometers for ions at lower m/z values. While earlier studies of oligonucleotides were hindered by the extensive sodium adduction, we sought to explore the advantages of low buffer concentrations by the use of microdcialysis. A sample containing 60 $\mu$M d(pT)18 in 10 mM $NH_4OAc$ and 100 mM NaCl was dialyzed against different concentrations of buffer and analyzed on-line by ESI-MS. FIGS. 13a, 13b, and 13c compare the mass spectra of this sample after on-line microdialysis using three different dialysis buffers: $H_2O$, 2.5 mM $NH_4OAc$ and 10 mM $NH_4OAc$. When pure $H_2O$ was used as dialysis buffer, desalting was incomplete, as indicated by the sodium adduct peaks (FIG. 13a). The main charge states were 7-, 8- and 9-. When the dialysis buffer was changed to 2.5 mM NH4OAc, greatly improved desalting was achieved with negligible sodium adduction. The observed charge states shifted slightly towards lower values and sensitivity was nearly unchanged (FIG. 13b). A further increase of dialysis buffer concentration to 10 mM more effectively removed the residual sodium adducts (FIG. 13c), however, a nearly 10-fold decrease in sensitivity compared to using 2.5 mM $NH_4OAc$ as dialysis buffer was observed. The charge states shifted to lower values significantly, and the decreased sensitivity is likely associated with the decreased transmission efficiency of the mass spectrometer at higher m/z.

It is apparent that despite the high desalting efficiency of microdialysis, the strongly associated sodium ions are not rapidly removed by dialyzing against pure $H_2O$. Cation exchange with $NH_4^+$ at relatively higher buffer concentrations is required for effective sodium removal. The ion-pairing between sodium ion and the phosphate group in the oligonucleotide might account for the charge state shift. At high salt concentrations, a greater number of phosphate groups are ion-paired by sodium ions in solution and upon transfer into the gas phase. When the salt concentration decreases, more phosphate groups will be left "unprotected" and become charge carrying sites. Therefore, higher charge states are expected for low buffer concentrations. The sensitivity enhancement at lower buffer concentrations could be partially due to the more efficient MS detection for lower m/z ions, as mentioned earlier. Another reason may be attributed to the smaller number of charge carrying buffer species in solution when the buffer concentration is low, and consequently an increase in transfer efficiency of sample ion from solution to the gas phase. These results suggest that low dialysis buffer concentrations (~2.5 mM $NH_4OAc$) should be used in microdialysis of DNA samples for studies where higher buffer concentrations are not required, such as for single-stranded DNA.

Based on these experiments, we found that off-line microdialysis using 2.5 mM $NH_4OAc$ as dialysis buffer followed by the addition of piperidine and imidazole (25 mM final concentration of each base) provided the best combination thus far for the extremely challenging DNA sample cleanup problem for ESI-MS. The application of this technique for PCR products cleanup has also been demonstrated elsewhere 28. While the purpose of using low buffer concentrations was to increase sensitivity and extend oligonucleotide size amenable to MS, we observed the "melting" (i.e., loss) of duplex conformation in solution during microdialysis of PCR products using 2.5 mM $NH_4OAc$ as dialysis buffer. This observation was qualitatively consistent with the correlation of DNA melting with solution salt concentrations. Since the salt concentration in the DNA samples after microdialysis was only 2.5 mM $NH_4OAc$, the PCR products we studied should have melting temperatures lower than room temperature after microdialysis. The advantages of using microdtialysis to denature double-stranded DNA in solution and analyzing single-stranded DNA are discussed elsewhere 28. When the double-stranded DNA conformation is essential (e.g., in studies of non-covalent complexes with duplex DNA), higher dialysis buffer concentrations (>10 mM $NH_4OAc$) should be used.

Closure

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A microdialysis unit having
   (a) a capillary assembly having at least one dialysis tube with an inside diameter less than about 0.5 mm, said dialysis tube having opposite ends of a sample inlet and sample outlet attached to a non-porous inlet and outlet;
   (b) a shell surrounding said capillary assembly and forming an annular space therebetween, said non-porous inlet and outlet extending through said shell and extending beyond said shell, said shell further having a buffer inlet and buffer outlet; and
   (c) a first fluid within said dialysis tube, and a second fluid within said annulus; wherein a sample containing low molecular weight molecules passes said low molecular weight molecules to a buffer through said dialysis tube, said sample retaining an interfering amount of said low molecular weight molecules;
   wherein the improvement comprises:
      said first fluid is a solution of a biomolecular or high molecular weight sample having low molecular weight molecules therein flowing through said dialysis tube;

said second fluid is a buffer that flows through said buffer inlet into said annular space and out said buffer outlet, said buffer inlet placed near said sample outlet and said buffer outlet placed near said sample inlet, arranged so that said buffer flows in a counterflow relationship to said biomolecular sample; wherein said buffer is continuously refreshed as it flows through said shell while said biomolecular sample flows through said capillary assembly so that substantially all of said low molecular weight molecules pass from said solution through said dialysis tube and into said buffer, while substantially all of said high molecular weight biomolecules are retained and passed to said sample outlet.

2. The microdialysis unit as recited in claim 1, further comprising a heater for heating said microdialysis unit.

3. The microdialysis unit as recited in claim 1, wherein said buffer has a concentration of $NH_4OAc$ less or equal to 20 mM.

4. The microdialysis unit as recited in claim 3, wherein said buffer further comprises:

piperidine and imidazole added to the buffer resulting in a reduction of charge states and an increase in detection sensitivity.

5. The microdialysis unit as recited in claim 1, wherein said sample outlet is connected in-line with an electrospray ionization mass spectrometer.

6. The microdialysis unit as recited in claim 1, wherein said sample outlet is connected to a microcentrifuge tube or other off-line sample collector.

7. The microdialysis unit as recited in claim 1, wherein said dialysis tube has a molecular weight cutoff less than about 50,000 Da.

8. The microdialysis unit as recited in claim 1, wherein said biomolecular sample is introduced by direct infusion.

9. The microdialysis unit as recited in claim 1, wherein said biomolecular sample is introduced as a sample plug.

10. The microdialysis unit as recited in claim 1, wherein said sample has a flow rate of at least about 0.01 $\mu$L/min.

11. The microdialysis unit as recited in claim 9, wherein said buffer has a flow rate of at least about 500 $\mu$L/min.

* * * * *